(12) United States Patent
Bouwman et al.

(10) Patent No.: US 12,193,793 B2
(45) Date of Patent: Jan. 14, 2025

(54) METHOD AND APPARATUS FOR QUANTITATIVE HEMODYNAMIC FLOW ANALYSIS

(71) Applicant: PIE MEDICAL IMAGING B.V., Maastricht (NL)

(72) Inventors: Chris Bouwman, Oirsbeek (NL); Dennis Koehn, Voerendaal (NL); Jean-Paul Aben, Limbricht (NL)

(73) Assignee: PIE MEDICAL IMAGING B.V., Maastricht (NL)

( * ) Notice: Subject to any disclaimer, the term of this patent is extended or adjusted under 35 U.S.C. 154(b) by 676 days.

(21) Appl. No.: 17/366,274

(22) Filed: Jul. 2, 2021

(65) Prior Publication Data
US 2021/0338088 A1    Nov. 4, 2021

Related U.S. Application Data

(62) Division of application No. 16/438,955, filed on Jun. 12, 2019, now Pat. No. 11,083,377.

(60) Provisional application No. 62/685,651, filed on Jun. 15, 2018.

(51) Int. Cl.
| | |
|---|---|
| *G06T 7/00* | (2017.01) |
| *A61B 5/00* | (2006.01) |
| *A61B 5/02* | (2006.01) |
| *A61B 5/021* | (2006.01) |
| *A61B 5/107* | (2006.01) |
| *G06T 7/62* | (2017.01) |
| *G06T 11/00* | (2006.01) |
| *A61B 5/0285* | (2006.01) |

(52) U.S. Cl.
CPC .......... *A61B 5/02007* (2013.01); *A61B 5/021* (2013.01); *A61B 5/107* (2013.01); *A61B 5/7278* (2013.01); *G06T 7/0012* (2013.01); *G06T 7/62* (2017.01); *G06T 11/003* (2013.01); *A61B 5/0285* (2013.01); *G06T 2207/10116* (2013.01); *G06T 2207/30104* (2013.01); *G06T 2210/24* (2013.01); *G06T 2210/41* (2013.01)

(58) Field of Classification Search
None
See application file for complete search history.

(56) References Cited

U.S. PATENT DOCUMENTS

| | | | | |
|---|---|---|---|---|
| 2007/0053555 | A1* | 3/2007 | Ooi | A61B 6/461 382/128 |
| 2015/0313479 | A1* | 11/2015 | Stigall | A61B 5/02007 600/467 |
| 2018/0296169 | A1* | 10/2018 | Ichihara | G16H 50/30 |
| 2018/0353241 | A1* | 12/2018 | Tu | A61B 8/5223 |
| 2020/0098124 | A1* | 3/2020 | Wang | A61B 5/7267 |

(Continued)

*Primary Examiner* — Sean M Conner
(74) *Attorney, Agent, or Firm* — Dean D. Small; The Small Patent Law Group, LLC

(57) ABSTRACT

Computer-implemented methods and systems are provided for quantitative hemodynamic flow analysis, which involves retrieving patient specific image data. A 3D reconstruction of a vessel of interest can be created from the patient specific image data. Geometric information can be extracted from the 3D reconstruction. A lesion position can be determined. Patient specific data can be obtained. Hemodynamic results can be calculated based on the geometric information, the lesion position and the patient specific data.

31 Claims, 30 Drawing Sheets

Grey zones contains discarded datapoint for healthy fit (2603)

(56) References Cited

U.S. PATENT DOCUMENTS

2021/0085397 A1* 3/2021 Passerini ................ G16H 50/20
2022/0164950 A1* 5/2022 Aben ..................... G16H 50/30

* cited by examiner

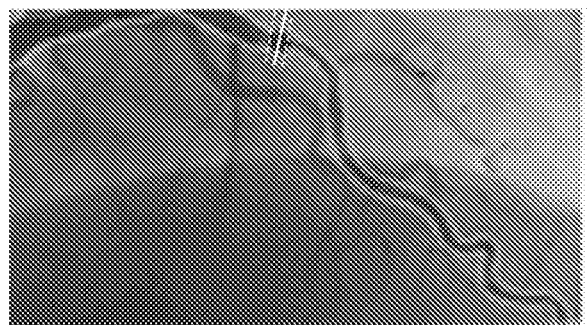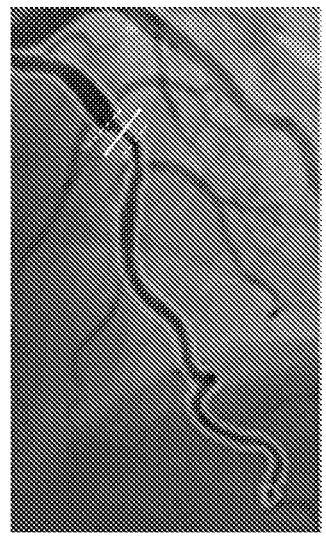
FIG. 8A　　　　　　　　　FIG. 8B
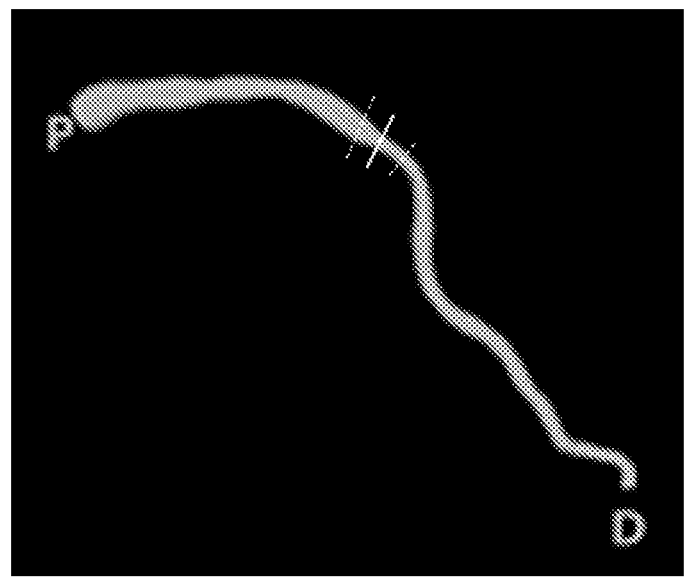
Fig. 8C

Grey zones contains discarded datapoint for healthy fit (2603)

METHOD AND APPARATUS FOR QUANTITATIVE HEMODYNAMIC FLOW ANALYSIS

CROSS-REFERENCE TO RELATED APPLICATIONS

The present application is a divisional application of U.S. application Ser. No. 16/438,955, filed 12 Jun. 2019, entitled "METHOD AND APPARATUS FOR QUANTITATIVE HEMODYNAMIC FLOW ANALYSIS," which claims priority to U.S. Application No. 62/685,651, entitled "METHOD AND APPARATUS FOR QUANTITATIVE HEMODYNAMIC FLOW ANALYSIS," filed on 15 Jun. 2018, both of which are expressly incorporated herein by reference in their entirety.

BACKGROUND

1. Field

The present disclosure relates to the technical field of medical imaging, particularly angiography imaging, although it can find application in any field where there is the need to quantify flow hemodynamics in obstructed or partially obstructed conduits such as in nondestructive testing applications.

2. State of the Art

Cardiovascular disease (CVD) is one of the leading causes of deaths worldwide. CVD generally refers to conditions that involve narrowed or blocked blood vessels that can lead to reduced or absent blood and therefore oxygen supply to the sections distal to the stenosis, resulting in, for instance, chest pain (angina) and ischemia. A very important aspect in the prevention and treatment of CVD is the functional assessment of such narrowed or blocked blood vessels.

Presently, X-ray angiography is the imaging modality used during treatment of stenotic (narrowed) coronary arteries by means of a minimally invasive procedure also known as percutaneous coronary intervention (PCI). During PCI, a (interventional) cardiologist feeds a deflated balloon or other device on a catheter from the inguinal femoral artery or radial artery up through blood vessels until they reach the site of blockage in the artery. X-ray imaging is used to guide the catheter threading. PCI usually involves inflating a balloon to open the artery with the aim to restore unimpeded blood flow. Stents or scaffolds may be placed at the site of the blockage to hold the artery open.

X-ray angiography is also a standard imaging technique for anatomical assessment of the coronary arteries and the diagnosis of coronary artery disease, known as x-ray diagnostics angiography. Even when the geometric dimensions of a stenosis are quantified by means of two-dimensional (2D) quantitative coronary analysis tools (QCA), as for instance taught by Gronenschild E, et al. in "*CAAS II: A Second Generation system for Off-Line and On-Line Quantitative Coronary Angiography*", Cardiovascular Diagnosis 1994; 33: 61-75, or by means of three-dimensional (3D) QCA, for instance as thought by Yoshinobu Onuma et al. in "*A novel dedicated 3-dimensional quantitative coronary analysis methodology for bifurcation lesions*", EuroIntervention 2011; 6:1-00, the translation of anatomic lumen reduction to hemodynamic stenosis severity is not straightforward since functional coronary lesion severity depends on coronary hemodynamics. This poor relation between anatomical and functional severity of coronary stenosis was also shown using new and promising non-invasive techniques using multidetector computed tomography coronary angiography (CCTA) by Sarno G et al. in "*On the inappropriateness of noninvasive multidetector computed tomography coronary angiography to trigger coronary revascularization: a comparison with invasive angiography*", JACC Cardiovasc Interv. 2009 June; 2(6):550-7.

For intermediate coronary lesions, defined as luminal reduction of 30-70% for instance, it is not always obvious if the stenosis is a risk for the patient and if it is desired to take action. Overestimation of the severity of the stenosis can cause a treatment which in hindsight would not have been necessary. Therefore exposing the patient to risks that are not necessary. Underestimation of the stenosis, however, could induce risks because the patient is left untreated when the stenosis is in reality severe. Especially for these situations it is desired to have an additional functional assessment to aid in a good decision making.

Fractional Flow Reserve (FFR) has been used increasingly over the last 15-20 years as a method to identify and effectively target the coronary lesion most likely to benefit from PCI. FFR is defined as the ratio between the pressure distal to a coronary lesion to the pressure before the coronary lesion (the aortic pressure) as measured during hyperemia. FFR is a technique used to measure pressure differences across a coronary artery stenosis to determine the likelihood that the stenosis impedes oxygen delivery to the heart muscle. The technique involves percutaneously inserting a pressure-transducing wire inside the coronary artery guided by x-ray coronary angiography and measuring the pressure behind (distal to) and before (proximal to) the lesion. This is best done in a hyperemic state because in the case of maximum hyperemia, blood flow to the myocardium is proportional to the myocardium perfusion pressure. FFR therefore provides a quantitative assessment of the functional severity of the coronary lesion as described by Pijls et al. in "*Measurement of Fractional Flow Reserve to Assess the Functional Severity of Coronary-Artery Stenoses*," N Engl J Med 1996, 334:1703-1708. Due to the invasive nature of measure FFR with a pressure-transducing wire, this technique is also called invasive FFR.

Although the European Society of Cardiology (ESC) and the American College of Cardiology/American Heart Association (ACC/AHA) guidelines recommend the use of FFR in patients with intermediate coronary stenosis (30-70%), visual assessment, whether or not supported by QCA, of X-ray coronary angiograms alone is still used in over 90% of procedures to select patients for percutaneous coronary intervention (Kleiman et al, "*Bringing it all together: integration of physiology with anatomy during cardiac catheterization*," J Am Coll Cardiol. 2011; 58:1219-1221).

Several factors can contribute to the low uses (10%) of (invasive) FFR during PCI even though with the strong evidence base and recommendations from the guidelines. First, decisions regarding the mode of revascularization are usually made at the time of invasive x-ray coronary angiography, but this is limited specifically to PCI operators, working in an interventional catheter laboratory, with the time and facilities to perform FFR. Second, the procedure is prolonged, and invasive FFR associated with the additional cost of a pressure wire which can only be used once. Measuring FFR requires invasive catheterization with the associated cost and procedure time. Also, in order to induce (maximum) hyperemia, additional drug infusion (adenosine or papaverine) is required, which is an extra burden for the patient. Third, many operators remain confident that their own visual assessment is physiologically accurate, allied to a misconception that multiple visual assessments (e.g., in a "Heart Team" setting) or a prior non-invasive test of ischemia improve their accuracy. Finally, despite the FAME (Fractional Flow Reserve Versus Angiography for Multivessel Evaluation) trial data (Tonino P. et al., "*Fractional flow reserve versus angiography for guiding percutaneous coronary intervention*", N Engl J Med. 2009 Jan. 15; 360(3): 213-24), some clinicians remain skeptical of the value of PCI in the context of stable coronary artery disease, which reduces enthusiasm for invasive FFR assessment.

Kirkeeide and co-workers introduced a method to calculate coronary flow reserve (CFR) by using geometrical information extracted from 2D QCA as described in Kirkeeide et al., "*Assessment of coronary stenoses by myocardial perfusion imaging during pharmacologic coronary vasodilation. VII. Validation of coronary flow reserve as a single integrated functional measure of stenosis severity reflecting all its geometric dimensions*", J Am Coll Cardiol. 1986 January; 7(1):103-13. Limitations of the Kirkeeide approach are amongst others the use of 2D geometrical information and therefore being less accurate. CFR is defined as the ratio of maximum coronary blood flow through a coronary artery to its resting coronary blood flow. Moreover, CFR is not described in medical guidelines, in contrary to FFR.

There is therefore a need for a method that delivers the benefits of physiological lesion assessment to every cardiologist without the practical drawbacks that are associated with invasive FFR. A method, that reduces costs and improves patient management, is computed fractional flow reserve (cFFR) which uses sophisticated computation techniques allied to anatomical models based upon coronary imaging. Computational fluid dynamics (CFD) computations are used to calculate the coronary blood flow circulation and derive the fractional flow reserve resulting from a coronary lesion. Several studies have been performed in the field of cFFR by means of CFD. For instance, Taylor et al., "*Computational Fluid Dynamics Applied to Cardiac Computed Tomography for Noninvasive Quantification of Fractional Flow Reserve*", Journal of the American College of Cardiology, Vol. 61, No. 22, 2013, and U.S. Pat. No. 8,315,812, describe a method for calculating FFR based on CCTA, which we refer to as FFRCT. This technology uses CFD applied to CCTA after semi-automated segmentation of the coronary tree including a part of the ascending aorta covering the region in which both the left coronary artery as well as the right coronary artery emanate. Three-dimensional (3D) blood flow and pressure of the coronary arteries are simulated, with blood modelled as an incompressible Newtonian fluid with Navier-Stokes equations and solved subject to appropriate initial and boundary conditions with a finite element method on parallel supercomputer. The FFRCT is modeled for conditions of adenosine-induced hyperemia without adenosine infusion. This process is computationally complex and time-consuming and may require several hours. Furthermore, FFRCT uses non-invasive CCTA which is not the imaging modality used during PCI or diagnostic x-ray angiography.

In order to keep the computational demands on a feasible level a reduced model can be used in the calculation. That is, sections of the coronary tree can be represented by a one-dimensional network or zero-dimensional (lumped) model. This multi-scale approach was adopted by Kim et al., "*Patient-specific modeling of blood flow and pressure in human coronary arteries*", Annals of Biomedical Engineering 38, 3195-3209, 2010 to compute physiologically realistic pressure and flow waveforms in coronary vessels at baseline conditions. Based on 3D coronary geometry derived from CCTA, CFD simulations were coupled with an analytical 1D model of the circulation and a lumped-parameter model of the coronary resistance. However some underlying assumptions of these methods provide some limitations as described by Wijngaard et al., "*3D imaging of vascular networks for biophysical modeling of perfusion distribution within the heart*", Journal of Biomechanics 46 (2013) 229-239.

cFFR approached which uses CFD can also be applied on 3D coronary anatomical models derived from x-ray angiography. For instance, Morris et al., "*Virtual fractional flow reserve from coronary angiography: modeling the significance of coronary lesions: results from the VIRTU-1 (VIRTUal Fractional Flow Reserve From Coronary Angiography) study*", JACC Cardiovasc Interv. 2013 February; 6(2): 149-57, applied CFD to anatomical coronary model based on 3D coronary reconstruction from x-ray coronary angiography. Patient specific downstream boundary conditions were developed and applied to the arterial outlet(s) using a Windkessel model. A Windkessel model is an electrical analogue of arterial vasculature, in which the downstream resistance was calculated from the pressure and flow over the heart cycle. Such a techniques can in principle be used during PCI, but practically it will not be used due to the long computation time (24 hours).

A different approach to reduce the computation time required by CFD, is introduced in WO2015/058044. In this work, a method is disclosed to assess the FFR by means of a machine learning system which is based on features extracted from the anatomical three-dimensional coronary geometry. The machine-learning is trained by using geometric extracted features from synthetically generated 3D stenosis geometries and FFR values corresponding to the synthetically generated 3D stenosis computed by use of CFD. After the learning phase, the system predicts the FFR based on extraction of the same features of an unseen anatomical three-dimensional coronary geometry which is for instance extracted from CCTA by means of image segmentation methods.

However, machine learning techniques also have some disadvantages as described by Brynjolfsson, E. & McAfee, A, "The business of artificial intelligence: What it can and cannot do for your organization", Harvard Business Review 2017.

One noticeable limitation of machine learning is its susceptibility to errors. Errors are inevitable and diagnosing and correcting them can be difficult because the underlying structure can be complex. Furthermore the solution may be far from optimal if the conditions under which the system was trained change, for instance when the clinician uses a different imaging protocol.

Another limitation of machine learning is that it learns through historical data. The bigger the data and the longer it is exposed to this data, the better the algorithm will perform. However, in the case of medical imaging it is difficult to provide a very large dataset as new techniques are not performed in abundance.

Another limitation of machine learning is the lack of verifiability. Brynjolfsson and McAfee said that machine learning deals with statistical truths rather than literal truths. In situations that are not included in the historical data, it will be difficult to prove with certainty that the predictions made by machine learning are correct in all scenarios.

There is thus the need for a method that assessed the functional hemodynamic severity of a coronary lesion that can be used during a percutaneous coronary intervention procedure which fits into the clinical workflow of such a procedure.

SUMMARY

Computer-implemented methods and systems are provided for quantitative hemodynamic flow analysis, which involves retrieving patient specific image data. A 3D reconstruction of a vessel of interest can be created from the patient specific image data. Geometric information can be extracted from the 3D reconstruction. A lesion position can be determined, and patient specific data can be obtained. Hemodynamic results can be calculated based on the geometric information, the lesion position and the patient specific data.

In embodiments, at least one of the operations is performed by one or more processors executing program instructions.

In embodiments, the vessel of interest represents a subset of a coronary tree, and the calculation of the hemodynamic results can be based in part on an assumption that the coronary tree exhibits a constant healthy velocity throughout.

In embodiments, the calculation of the hemodynamic results can utilize a velocity that is independent of location within the coronary tree.

In embodiments, the determination of the lesion position can be based, at least in part, on calculation of a flow pattern parameter indicative of whether flow is laminar or turbulent. The flow pattern parameter can be calculated based on the geometry information extracted from the 3D reconstruction. For example, the flow pattern parameter can be a Reynolds number. The flow pattern parameter can be calculated based on an estimate of a healthy geometry along the vessel of interest. The estimate of the healthy geometry can be an estimate of at least one of diameter or area at a segment of the vessel of interest proximate to the lesion position.

In embodiments, the determination of the lesion position can involve identifying variations in blood velocity along the vessel of interest wherein the variations are caused by a presence of vessel narrowing. The variation in the blood velocity can be calculated based on the geometric information extracted from the 3D reconstruction and/or an estimate of a healthy geometry along the vessel of interest (e.g., an estimate of at least one of diameter or area).

In embodiments, the methods and systems can be configured to calculate a gravitational pressure gradient due to a different in altitude along proximal and distal ends of the vessel of interest. The hemodynamic results can be calculated in part based on the gravitational pressure gradient.

In embodiments, the calculation of the hemodynamic results can involve a myocardial blush calculation to determine a status of a myocardium microvasculature.

In embodiments, the creation of the 3D reconstruction can involve one or more of the following operations:
  selecting an image sequence, angulation and rotation from the patient specific image data;
  determining first and second select image frames from the patient specific image data;
  detecting luminal boundaries in the first and second select image frames;
  determining first and second select image projections; and
  creating the 3D reconstruction from the first and second select image projections.

In embodiments, the extraction of the geometric information can be configured to avoid geometric inaccuracies due to at least one of a) out of plane magnifications errors and b) foreshortening errors.

In embodiments, the methods and systems can be configured to involve one or more of the following operations:
  calculating a virtual pullback of a pressure drop along a centerline of the vessel of interest within the 3D reconstruction, wherein the centerline comprises a number of centerline points between first and second locations, the centerline points representing at least a portion of the geometrical information of the 3D reconstructed vessel of interest;
  calculating a virtual pullback curve;
  utilizing the geometrical information of a segment to calculate a pressure drop and vessel FFR value between the first and second location; and
  adding the pressure drop and vessel FFR value to pullback curve data corresponding the second location.

In embodiments, the determination of the lesion position can involve at least one of the following operations:
  automatically fitting a line through diameter or area data points along the vessel of interest, the vessel of interest including a vessel narrowing segment at the lesion position and a health vessel segment that is at least one of distal and/or proximal to the lesion position;
  obtaining an estimate of a healthy vessel diameter or area along the vessel of interest by fitting a line through diameter or area data points excluding the vessel narrow segment along the vessel of interest;
  obtaining an estimate of a vessel narrowing diameter or area along the vessel narrowing segment; and
  calculating a diameter or area ratio of the i) vessel narrowing diameter or area with respect to ii) the healthy vessel diameter or area.

In embodiments, the lesion position can be determined based on the diameter ratio or area.

The methods can be part of an imaging workflow (such as an X-ray angiographic imaging workflow) that employs an imaging system (such as an X-ray angiographic imaging system) to obtain one or more patient specific image sequences.

Additional aspects, embodiments, objects and advantages of the disclosed methods may be understood with reference to the following detailed description taken in conjunction with the provided drawings.

BRIEF DESCRIPTION OF THE DRAWINGS

FIGS. 8A-8C show an example of the restriction of lesion position determination in 2D.

DETAILED DESCRIPTION OF ILLUSTRATIVE EMBODIMENT(S)

In order to provide the cardiologists a method that assessed the functional hemodynamic severity of a coronary lesion which can be used during a percutaneous coronary intervention procedure and does not suffer from the limitations contributing to the low uses of invasive FFR and associated to cFFR a new method is presented to calculate the FFR based on x-ray angiography, further referred to as vessel FFR.

Vessel FFR includes: a) calculation of FFR by using x-ray angiography, b) an analysis workflow which fits perfectly into the cardiologist's workflow during a percutaneous coronary intervention procedure or during an x-ray coronary angiography procedure and c) the total analysis time does not add procedure time.

Figure 1:
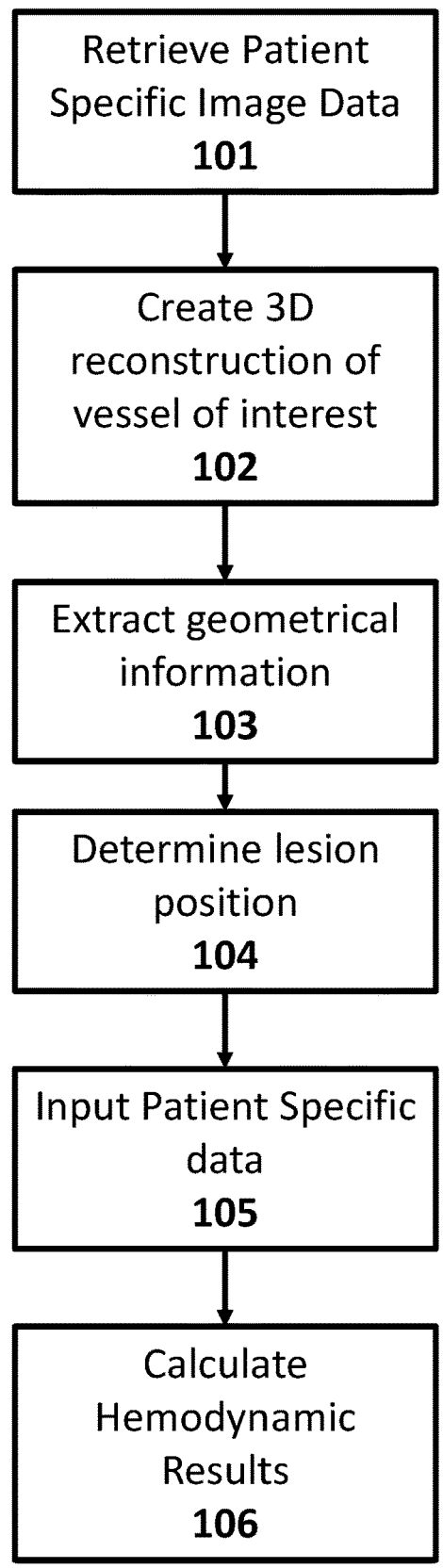
FIG. 1 shows a flow chart of a method for determining hemodynamic results in accordance with an embodiment herein.

FIG. 1 shows a flow chart illustrating the operations according to an embodiment of the present application. The operations employ an imaging system capable of acquiring and processing two-dimensional image sequences of a vessel organ (or portion thereof) or other object of interest. For example a single plane or bi-plane angiographic system can be used such as those manufactured, for example, by Siemens (Artis zee Biplane) or Philips (Allura Xper FD).

Figure 2:
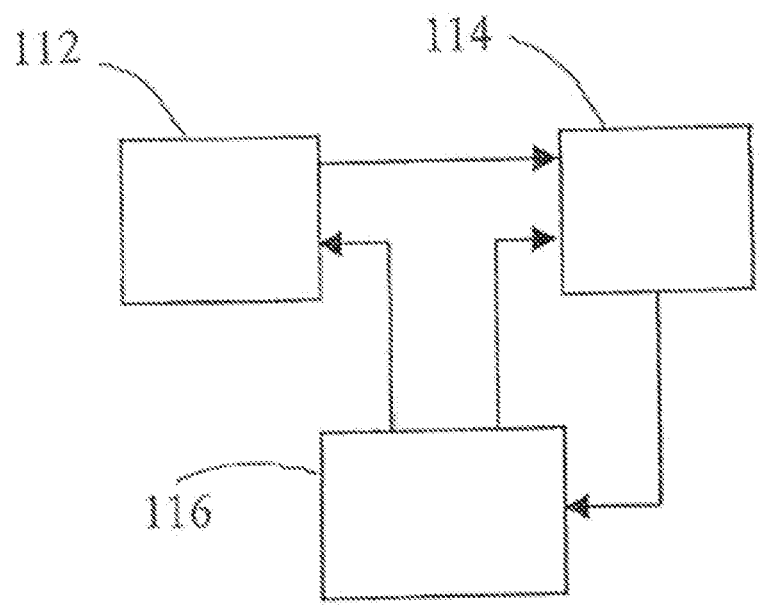
FIG. 2 shows a functional block diagram of an exemplary single plane angiographic system.

FIG. 2 is a functional block diagram of an exemplary single plane angiographic system, which includes an angiographic imaging apparatus 112 that operates under commands from user interface module 116 and will provide data to data processing module 114. The single plane angiographic imaging apparatus 112 captures a two-dimensional X-ray image sequence of the vessel organ of interest for example in the postero-anterior (PA) direction. The single plane angiographic imaging apparatus 112 typically includes an X-ray source and detector pair mounted on an arm of a supporting gantry. The gantry provides for positioning the arm of the X-ray source and detector at various angles with respect to a patient who is supported on a table between the X-ray source and detector. The data processing module 114 may be realized by a personal computer, workstation or other computer processing system. The data processing module 114 processes the two-dimensional image sequence captured by the single plane angiographic imaging apparatus 112 to generate data as described herein. The user interface module 116 interacts with the user and communicates with the data processing module 114. The user interface module 116 can include different kinds of input and output devices, such as a display screen for visual output, a touch screen for touch input, a mouse pointer or other pointing device for input, a microphone for speech input, a speaker for audio output, a keyboard and/or keypad for input, etc. The data processing module 114 and the user interface module 116 cooperate to carry out the operations of FIG. 1 as described below.

The operations of FIG. 1 can also be carried out by software code that is embodied in a computer product (for example, an optical disc or other form of persistent memory such as a USB drive or a network server). The software code can be directly loadable into the memory of a data processing system for carrying out the operations of FIG. 1. Such data processing system can also be physically separated from the angiographic system used for acquiring the images making use of any type of data communication for getting such images as input.

In this example it is assumed that the imaging system has acquired and stored at least one two-dimensional image sequence of an object of interest. Any image device capable of providing two-dimensional angiographic image sequences can be used for this purpose. For example a bi-plane or single plane angiographic system can be used such as those manufactured, for example, by Siemens (Artis zee Biplane) or Philips (Allura Xper FD).

At 101, the data processing module 114 is fed by at least one bi-dimensional image frame of the tree, or part of the tree, of conduits which have been obtained from different perspectives.

The data processing module at 114 generates a 3D reconstruction using a first image frame of 101 and a determined second image frame. At 103 the data processing module 114 makes calculations based on the 3D reconstruction to determine geometrical features of the conduits such as area, diameters, lengths, curvatures, centerlines or the like. These features are used to determine hemodynamic results.

At 104 the data processing module 114 determines a lesion position.

At 105, the data processing module 114 is fed by patient specific information such as aortic pressure in rest obtained invasively through an arterial line. At 106, the processing module 114 calculates hemodynamic results. The vessel FFR value for each segment of interest is, for example, calculated and shown on a display for the clinician.

An embodiment is now disclosed with reference to FIG. 1. The therein-depicted operations can, obviously, be performed in any logical sequence and can be omitted in parts. As it is an objective of the application to provide a select (e.g. optimal) workflow that can be used during the interventions, workflow example steps will also be referenced.

As can be seen in FIG. 1, the workflow comprises of number of steps.

Figure 3:
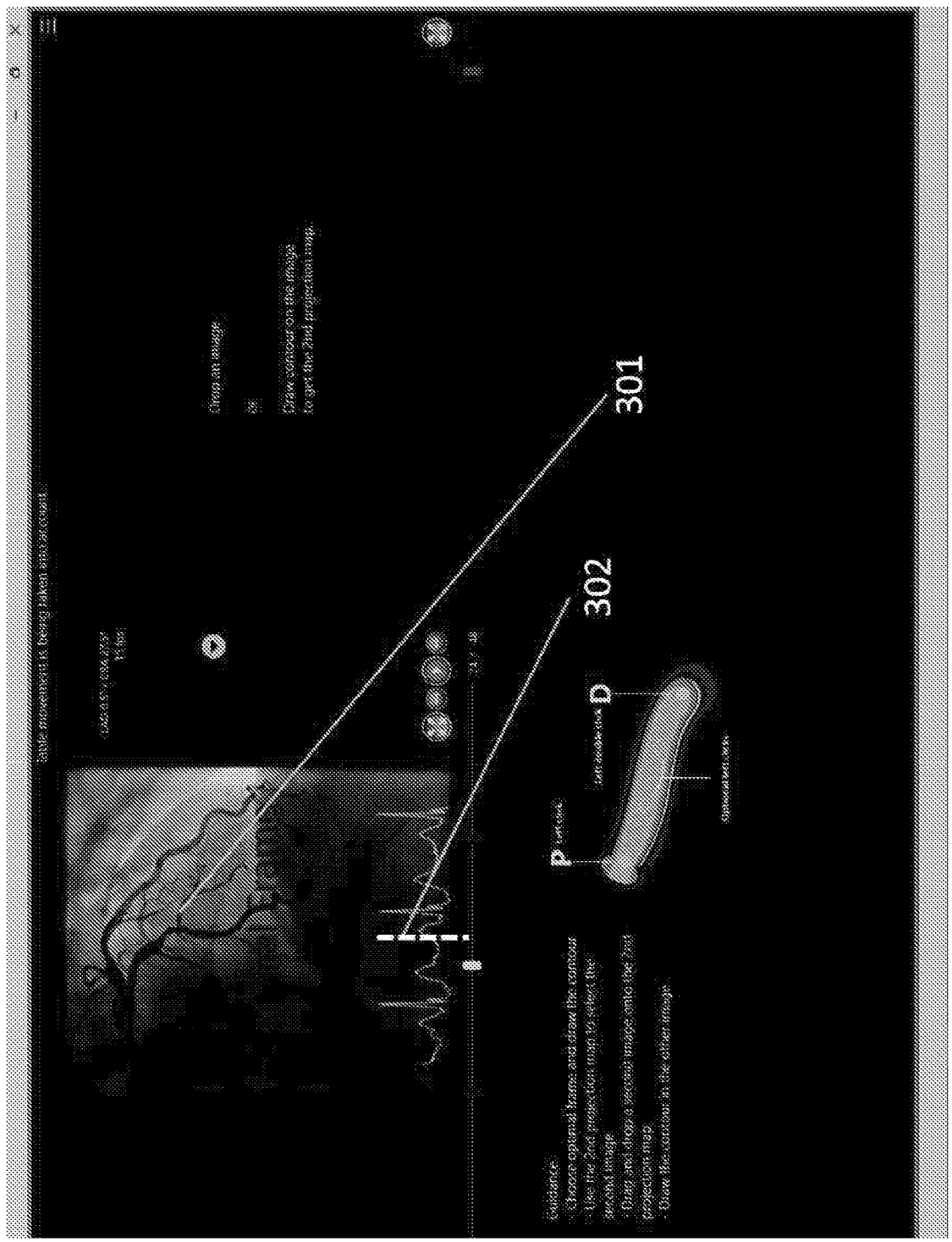
FIG. 3 shows an exemplary workflow screenshot to obtain the first image frame.

First patient specific image data is obtained as described in step 101 of FIG. 1. The patient specific image data is obtained during X-ray coronary angiography. This is a common step of a PCI intervention. Of the patient specific image data obtained during the X-ray coronary angiography one image sequence is selected by the clinician in which the coronary vessel of interest is clearly visible as can be seen in step 301 of FIG. 3 and step 401 of FIG. 4. The system then automatically defines the select (e.g. optimal) frame within the image sequence to initiate the analysis as described in step 402 of FIG. 4. An image sequence comprises multiple frames covering one or more phases of the cardiac cycle. Furthermore, during an acquisition at a certain moment in time the contrast agent injection is started resulting in visual enhancement of the coronary vessels. The select frame is defined as a frame with the least coronary motion in which contract liquid is present. The select frame can for instance be determined using the ECG signal of the patient (if present) as shown as reference 302 in FIG. 3.

Figure 4:
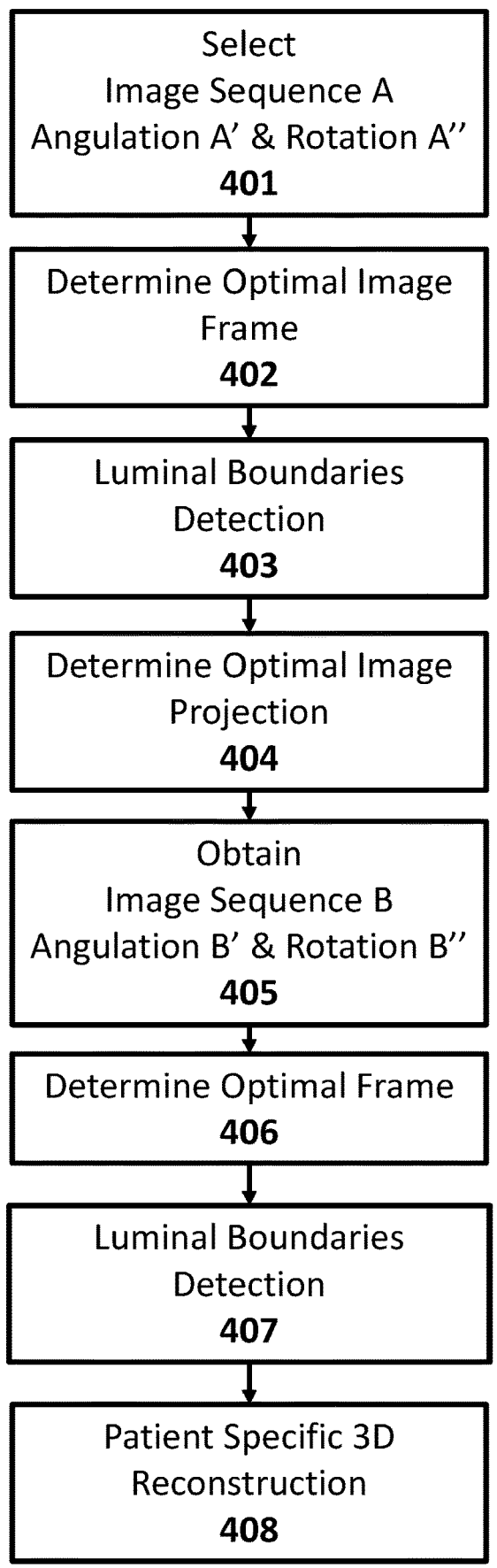
FIG. 4 shows a flow chart of a method for generating a 3D reconstruction.
Figure 5:
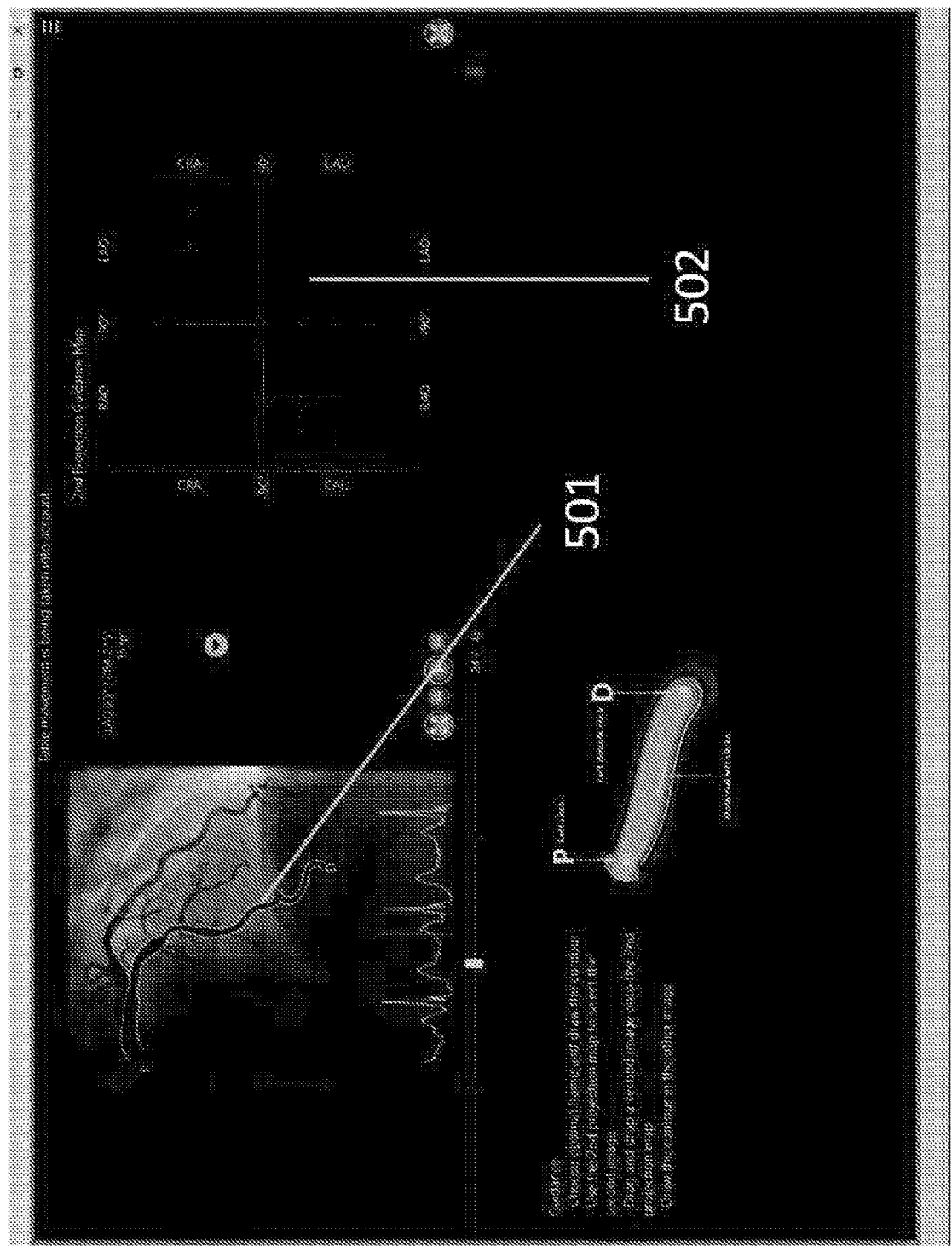
FIG. 5 shows an exemplary workflow screenshot with projection guidance.

In this selected frame, the luminal boundaries of the coronary vessel of interest are detected as described by step 403 of FIG. 4. This detection can for instance be done semi-automatically where the clinician identifies a proximal and a distal end point within the vessel of interest and the processor then automatically detects the luminal boundaries. The detected luminal boundaries can be seen in step 501 of FIG. 5. Optionally, the clinician can correct the detected luminal boundaries if needed.

One of the difficulties for a clinician during a standard PCI procedure or diagnostic x-ray angiography is selecting a second image projection that is desired (e.g. most optimal) in combination with the first image sequence to be used for generating an accurate 3D reconstruction, whereby an accurate 3D reconstruction is defined as a 3D reconstruction generated using the maximum amount of information concerning an object of interest. The two image sequences combined should contain as much information as possible regarding the object of interest. As the choice of this second image projection therefor largely determines the accuracy of the 3D reconstruction, it is important that it is chosen correctly. To simplify and facilitate this standard procedure step for the clinician, guidance is provided for the choice of the second image projection. This results in a color map, in which for each combination of rotation and angulation of the X-ray system a desired value (e.g. an optimal value) is shown using a corresponding color or grey value as can be seen in step 502 of FIG. 5. In the color map the whitest projection is the most optimal one, where the darkest projection is the less suitable one.

Using this color map the clinician can accurately and quickly determine which image projection is best suitable to obtain the second image sequence as described in step 404 of FIG. 4. This guidance for the clinician therefore can reduce standard procedure time.

Figure 6:
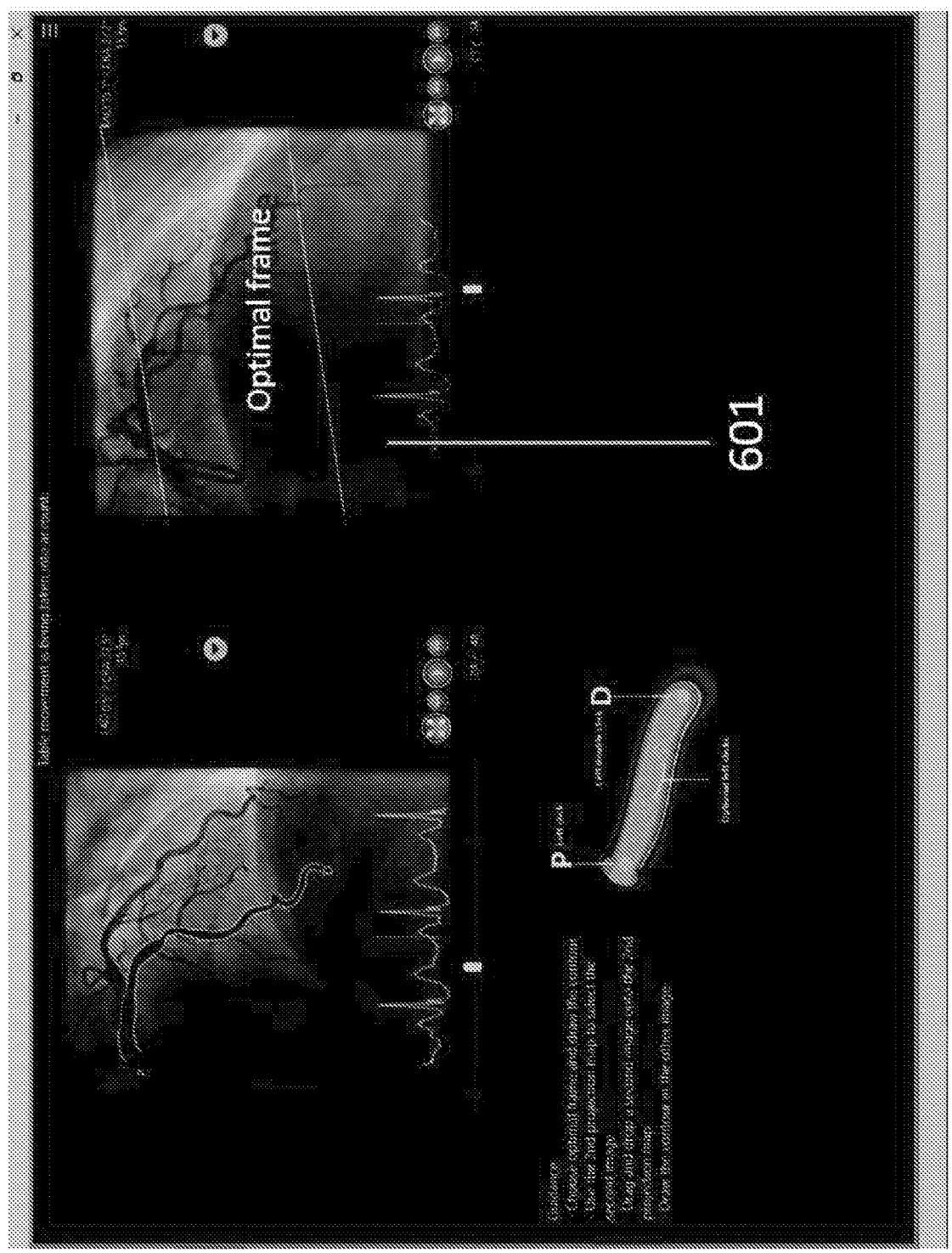
FIG. 6 shows an exemplary workflow screenshot with the obtained second image frame.

To obtain the image sequence corresponding to the selected image projection as described in step 405 of FIG. 4, the clinician can manually rotate the arm of the imaging system into the position that corresponds to the chosen second projection, or to simplify the procedure even more for the clinician, the C-arm control module 1710 can automatically rotate the arm of the imaging system to the calculated select projection. The obtained second image sequence is then presented to the clinician as shown in step 601 of FIG. 6.

Just as the first image sequence, the obtained second image sequence comprises of multiple frames covering one or more phases of the cardiac cycle. When a clinician for instance uses a single plane imaging system, the obtained second image sequence can consist of different cardiac phases than the first image sequence. The 3D reconstruction becomes more accurate when frames of the two images sequences are used to generate the 3D reconstruction that were obtained at the same cardiac phase. The system therefore also provides for the second image sequence the select image frame for detecting the vessel of interest as described in step 406 of FIG. 4.

Another aspect that can occur during an intervention is table movement. It is not uncommon that in between obtaining the first and second image sequence, the clinician has moved the patient table 1705 in order to for instance have a better overview during the procedure. However, table movement can also occur during image acquisition. When not taking table movement into account, inaccuracy can occur in the generation of the 3D reconstruction. Therefore X-ray system information, such as the distance between the X-ray tube and the X-ray detection panel, the distance between the X-ray tube and the C-arm isocenter, the position of the table rotation point relative to the C-arm isocenter, the 3D orientation of the C-arm and the adjustable table, both typically expressed in three angles, and finally the horizontal and vertical spacing of the pixels on the X-ray detector are taken into consideration during the 3D coronary reconstruction to compensate for table movement.

In the select frame of the second image sequence, the luminal boundaries are also detected (as shown in step 701 of FIG. 7 and described in step 407 of FIG. 4) using for instance the method as described for the first image frame.

Figure 7:
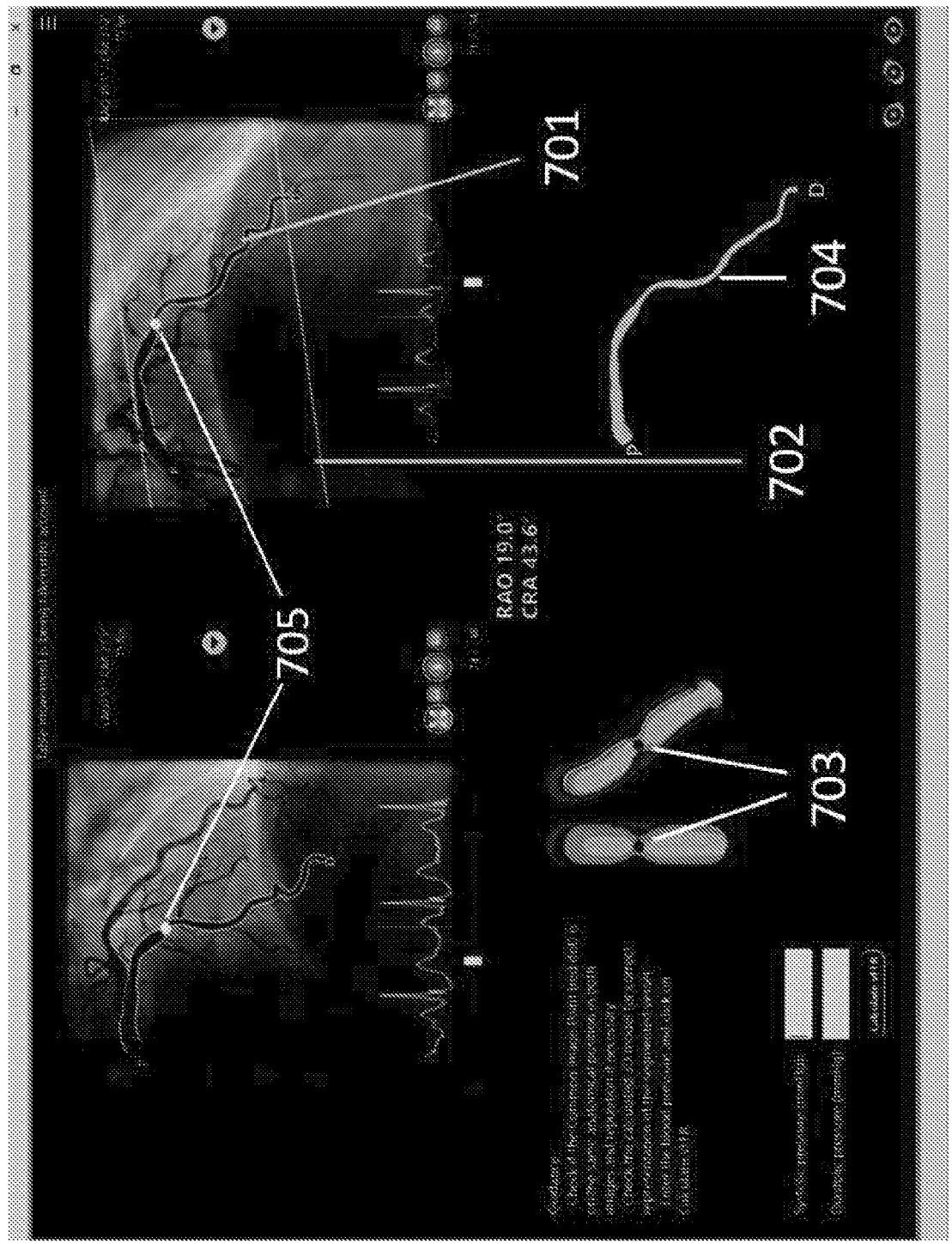
FIG. 7 shows an exemplary workflow screenshot with luminal boundaries and epi-polar lines.

To assist the clinician in indicating the vessel of interest in the second image frame so-called epi-polar lines as shown as reference 702 in FIG. 7 are shown on the second image frame. The epi-polar lines as shown in the second image frame represent the most proximal and distal position of the vessel as indicated in the first image frame following the viewing direction of the first image frame compared to the second image frame.

Additionally, a common image point (CIP) is automatically determined as can be seen in FIG. 7 as reference 705.

The CIP represents a common landmark in both image frames, indicating the same anatomical location as illustrated by 703 in FIG. 7. This CIP is needed to correct for a possible offset of the isocenter of the image frame. An incorrect CIP results in an inaccurate 3D reconstruction. Optionally the clinician can reposition the CIP if necessary.

After detection of the luminal boundaries in both image frames, the processor creates a 3D reconstruction of the vessel of interest represented by step 408 of FIG. 4. The metadata stored through the DICOM headers with the X-ray images should at least contain the following information: the distance between the X-ray tube and the X-ray detection panel, the distance between the X-ray tube and the C-arm isocenter, the position of the table rotation point relative to the C-arm isocenter, the 3D orientation of the C-arm and the adjustable table, both typically expressed in three angles, and finally the horizontal and vertical spacing of the pixels on the X-ray detector. Using this metadata, a complete geometric relation between the acquired images can be acquired that takes effects of repositioning the table into account.

While the derived geometric relations take the effects of table positioning into account, the actual position of the structure of interest may have changed due to other sources of motion. In the case of coronary arteries, these motion source included cardiac motion, respiratory motion, and patient motion relative to the table.

In order to compensate for the translation component of any remaining motion, a single point can be annotated (CIP as visible in FIG. 7 as reference 705) in all images that correspond the same physical point. Annotation of these points can either be done manually, or automatically. In the case where the structure of interest is a coronary artery, an example of an automatic annotation algorithm could be based on local diameter information extracted from the lumen boundary information. Using the annotated points to adjust the geometric relation between the images can be done as described in U.S. Pat. No. 7,155,046 entitled "Method of Determining Physical Parameters of Bodily Structures" issued to Aben et al.

Having a definition of the structure of interest within all images in addition to the geometric relation between all images, a 3D reconstruction of the structure of interest can then be reconstructed. A multitude of methods are described in existing art that are able to achieve this. Most of these methods are based on the concepts of epipolar constraint and triangulation. If the relative position of two views are known together with the projection of a 3D point in one of the images, an epipolar line in the other image can be defined that must contain the projected position of the same point. This is called the epipolar constraint. Having found the projected position on the epipolar line in the other images, the three-dimensional position of the point can then be reconstructed through a process called triangulation, as known to those skilled in the art. If the structure of interest definitions consist of vessel centerlines, the resulting 3D reconstruction will be a 3D centerline. If lumen boundaries are included in the structure of interest definitions, information of the local vessel diameters can be incorporated into the 3D reconstructed model. In this case a surface model of the vessel lumen can be created.

As described in step 102 of FIG. 1, the processor makes a patient specific 3D reconstruction of a subset of interest of the coronary tree which includes the coronary lesion(s) of interest using multiple two-dimensional images. An example of a 3D reconstruction is shown as reference 704 of FIG. 7.

Optionally, after generating the 3D reconstruction, the clinician can correct the luminal boundaries if needed. If the luminal boundaries have been corrected, a new 3D reconstruction will be generated automatically.

From the 3D reconstruction, geometric information can be extracted as described in step 103 of FIG. 1. This 3D geometric information can for example be the cross-sectional area and length of the vessel of interest along the centerline of the 3D reconstructed vessel of interest. From the cross-sectional area, the diameter can be determined for every point of the centerline. This diameter can for instance be derived from the cross-sectional area as the minimum, maximum of equivalent diameter. By using 3D geometric information instead of 2D, the measurements are more accurate. The length as determined in the 3D reconstruction is for instance not subjected to foreshortening. An example of extracted diameter results along the vessel of interest can be seen as reference 1001 of FIG. 10.

Once the 3D geometric information has been extracted, the lesion position is determined as described by step 104 of FIG. 1.

Figure 10:
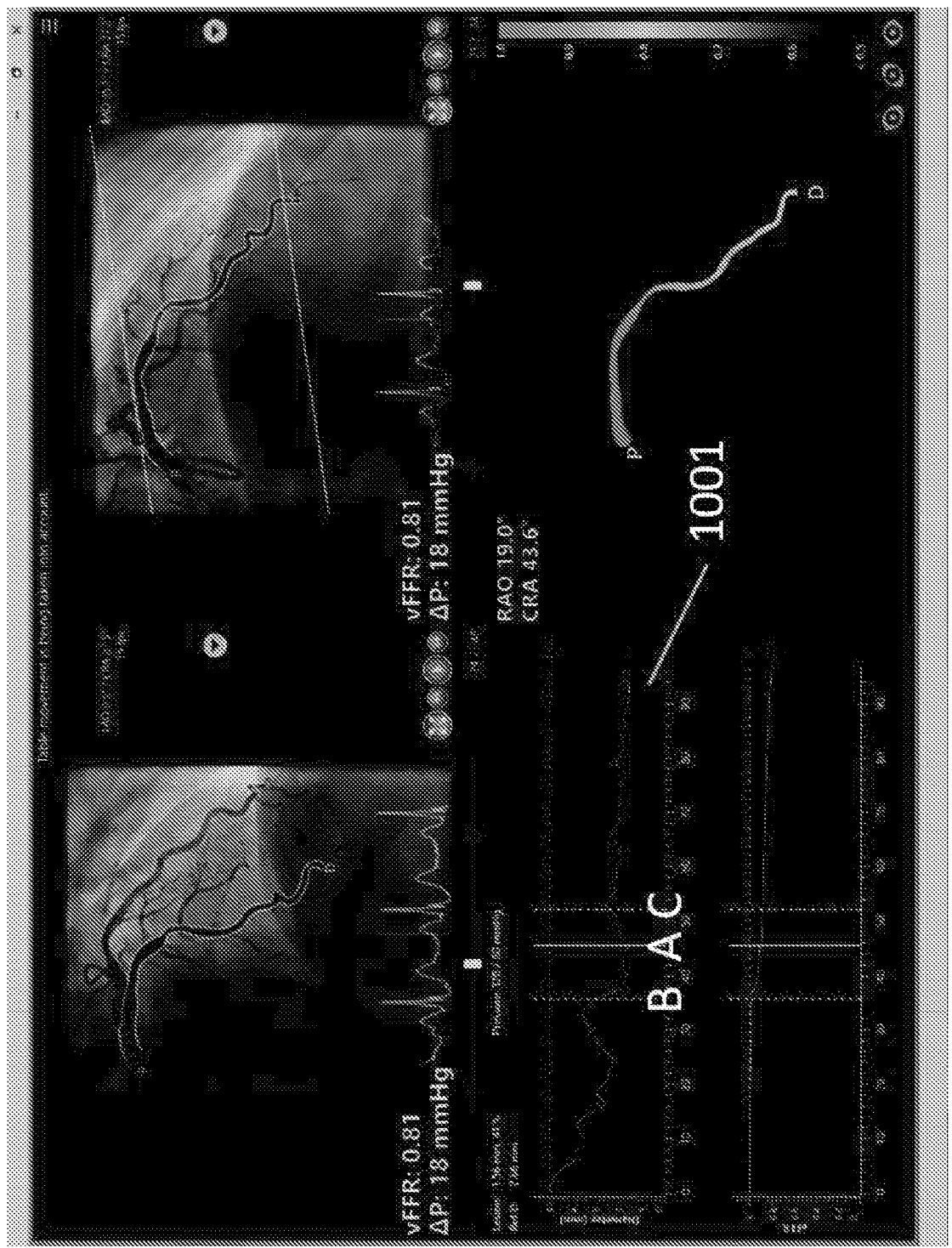
FIG. 10 shows an exemplary workflow screenshot that shows diameter results and lesion position.
Figure 16:
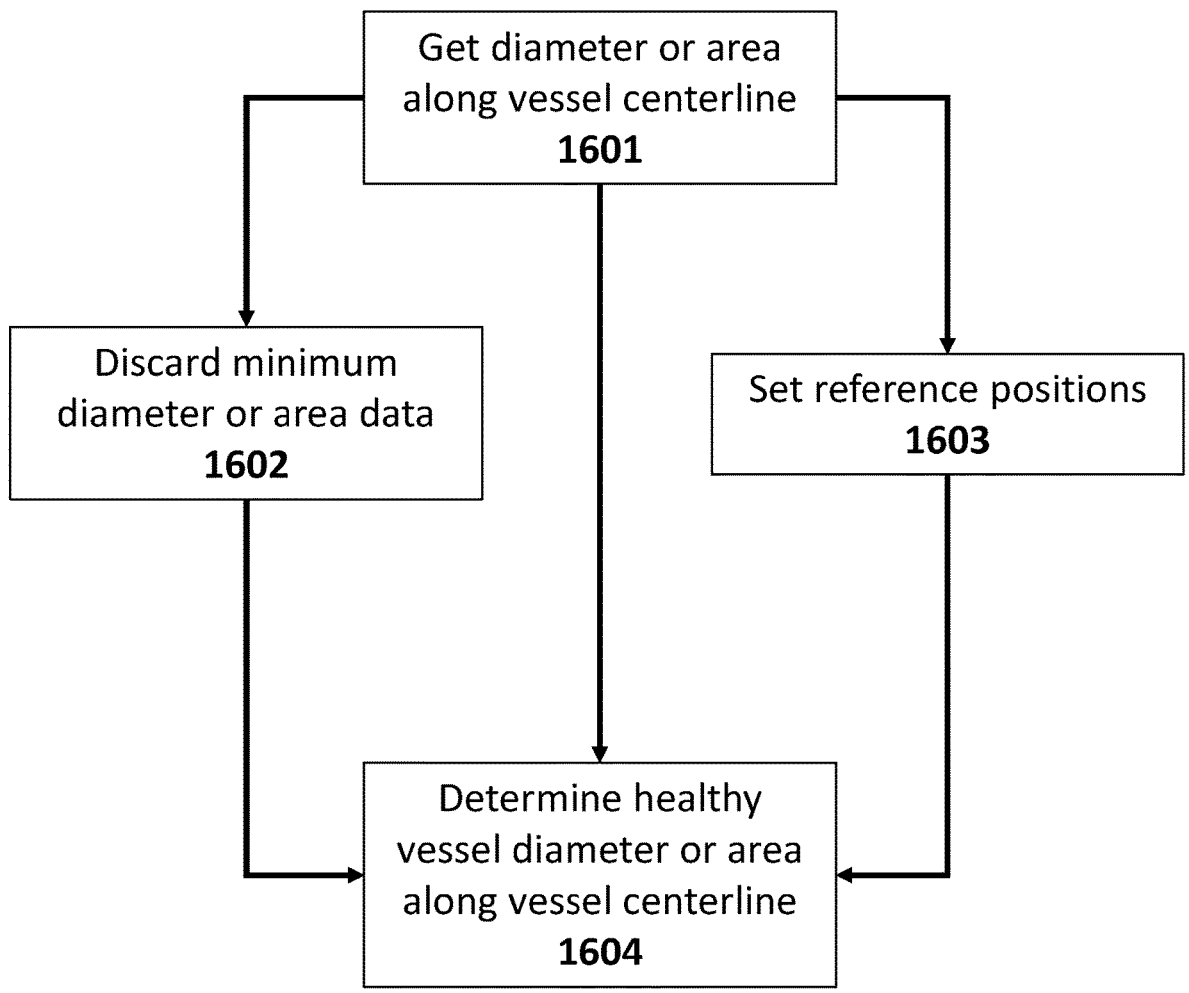
FIG. 16 shows a flow chart of a method to determine the healthy vessel diameter or area.
Figure 25:
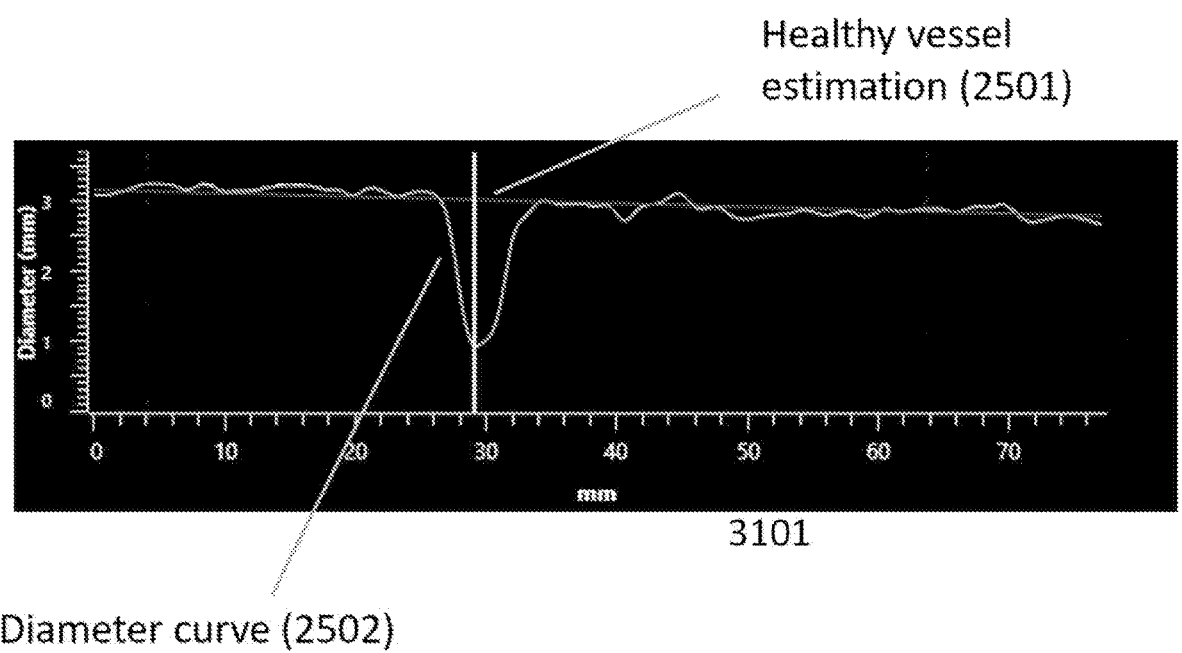
FIG. 25 illustrates an example of defining the healthy vessel estimation by fitting a straight line through the extracted geometrical information (e.g. diameter or area).

The lesion position comprises the position of the local minimum diameter (1001A) as well as corresponding obstruction borders proximal (1001B) and distal (1001C) to the position of the minimum diameter as shown in FIG. 10. The obstruction boundaries define the length of the stenotic lesion. The lesion position can be automatically determined as for instance taught by Gronenschild E, et al. in "*CAAS II: A Second Generation system for Off-Line and On-Line Quantitative Coronary Angiography*", Cardiovascular Diagnosis 1994; 33: 61-75. Using an automatic lesion position determination, the lesion position is defined directly by using the 3D reconstruction. This is more accurate than determining the lesion position in 2D as the 2D image frames can suffer from for instance foreshortening as described above, leading to an incorrect obstruction border placement. An example of the possible inaccuracy of a 2D lesion position determination can be seen in FIGS. 8A-8C. FIGS. 8A and 8B show the obstruction borders when determined in the 2D image frames. FIG. 8C shows the true obstruction borders as can be seen clearly in the 3D reconstruction. The lesion position determination can be based purely on the vessel geometry, for example the minimum diameter, the diameter ratio or area ratio of the vessel narrowing with respect to assumed healthy vessel diameter or area. To calculate the ratio of vessel narrowing, an estimation of the healthy vessel diameter or area along the vessel of interest is required. In FIG. 16 examples for estimation of the healthy vessel diameter or area are presented. Determination of the healthy vessel requires the diameter or area of the vessel of interest along the vessel centerline (1601 of FIG. 16). This geometrical information is extracted by step 103 of FIG. 1. In the first example all the diameter or area data along the vessel centerline is used (2502 of FIG. 25) and in step 1604 of FIG. 16 automatically a straight line is fitted through all the diameter or area data points as illustrated by 2501 of FIG. 25. This fitted line represents the healthy vessel diameter or area along the centerline of the vessel. Using this approach, the resulting healthy diameter or area line is based on all diameter or area values along the vessel and therefore includes also the diameters or areas within the diseased vessel part, this might cause a slight underestimation of the computed healthy diameter or area line.

Figure 26A:
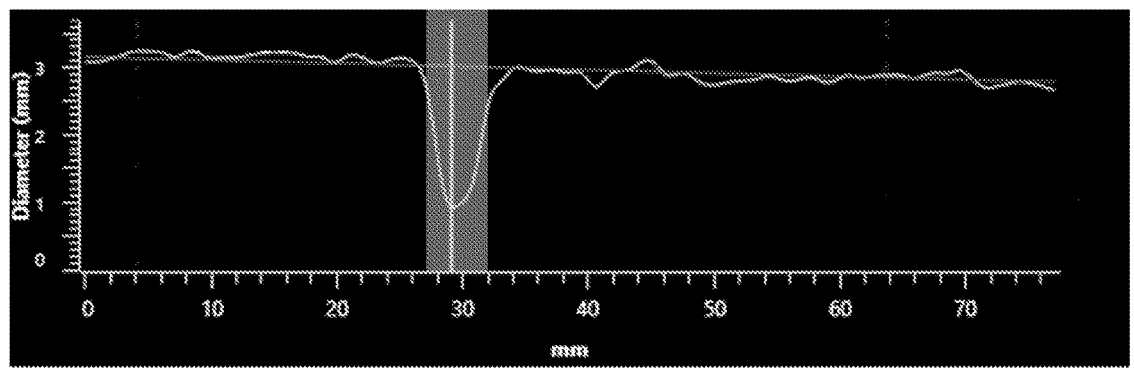
FIGS. 26A and 26B illustrate an example of defining the healthy vessel estimation by fitting a straight line through the designated geometrical information (e.g. diameter or area).
Figure 26B:
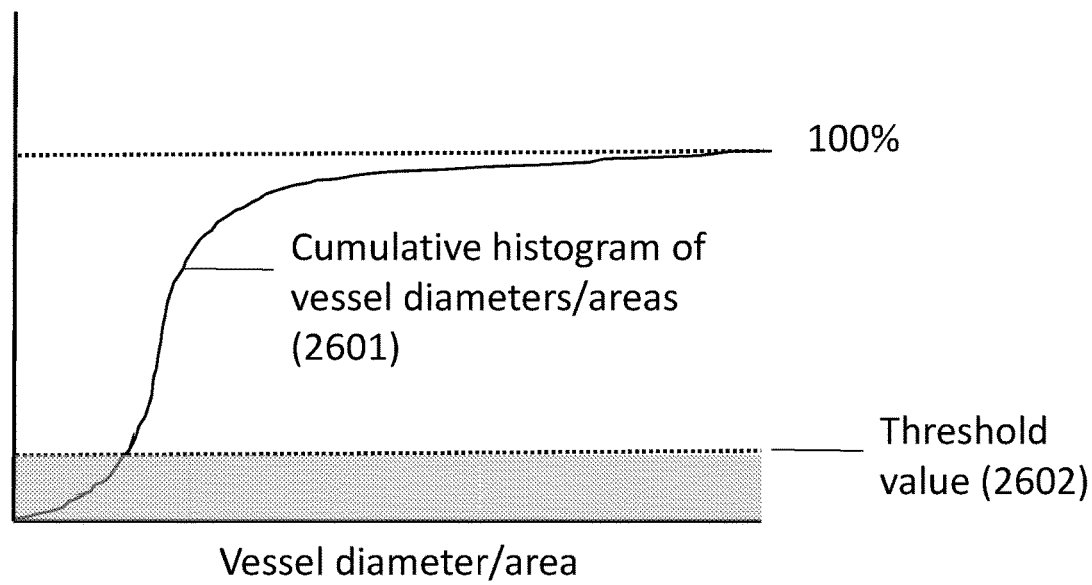

One approach to improve the reference diameter area computation would be by performing an optionally step 1602 of FIG. 16 in which deviating vessel diameters or vessel areas values are discarded from the diameter or area data. The determination of these deviating diameter or area values can be achieved by for example creating a cumulative histogram of all the vessel diameter or vessel area data points (2601 of FIG. 26B). Based on predefined or dynamic threshold value (2602 of FIG. 26B), the smallest vessel diameter or area values are discarded (2603 of FIG. 26A). Next, in step 1604 of FIG. 16, a straight line is fitted through the remaining diameter or area data points. This fitted line represents the healthy vessel diameter or area along the centerline of the vessel.

Figure 27:
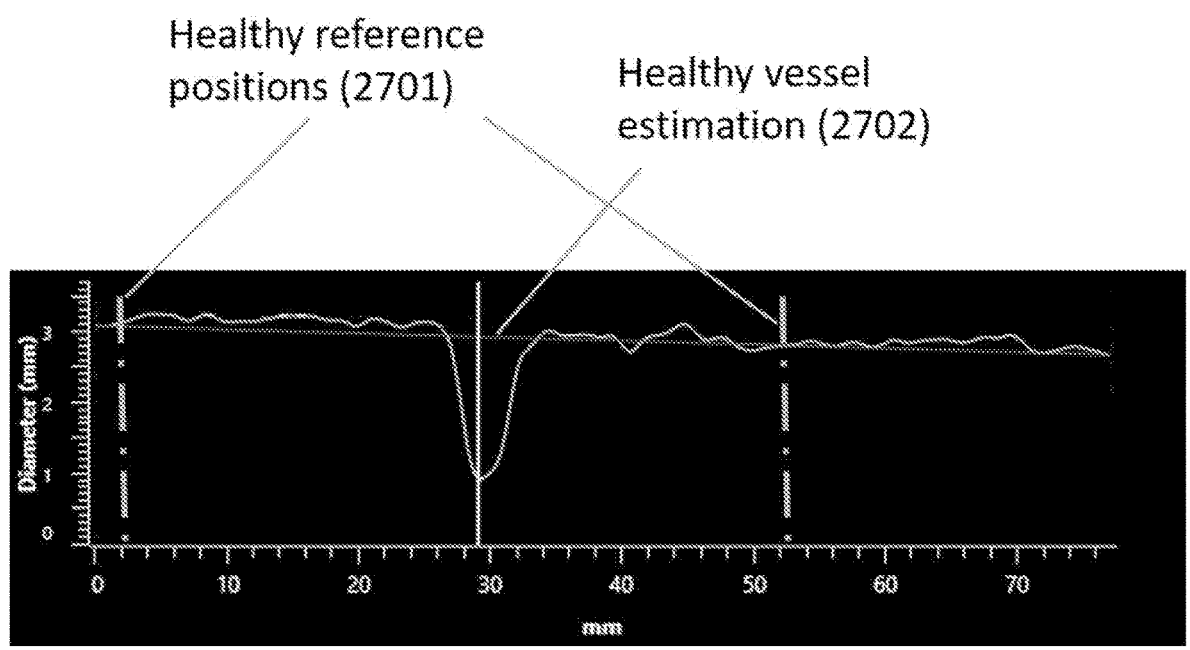
FIG. 27 illustrates an example of defining the healthy vessel estimation by fitting a straight line through manual reference positions.

Alternatively, in step 1603 of FIG. 16 manual reference positions are indicated by the physician according to the vessel diameter or area data (2701 of FIG. 27). The reference positions are identification of healthy vessel parts. Next, in step 1604 of FIG. 16 a straight line (2702 of FIG. 27) is fitted through the diameter or area data values at the reference positions as for instance taught by Gronenschild E, et al. in "*CAAS II: A Second Generation system for Off-Line and On-Line Quantitative Coronary Angiography*", Cardiovascular Diagnosis 1994; 33: 61-75. This fitted line represents the healthy vessel diameter or area along the centerline of the vessel.

Optionally, the clinician is able to define a different lesion position in the vessel by manually selecting this region. The selection of the lesion position can be done in the generated diameter graph (FIG. 10, 1001) or a 2D angiographic image or directly in the 3D reconstruction.

Alternatively, more than one lesion position can be selected in the vessel of interest. The processor/system determines another region of interest that also shows a local narrowing of the vessel lumen. Alternatively, the clinician can manually select another lesion position.

Alternatively, there is no lesion position defined by the clinician or determined automatically, because there is no local narrowing of the vessel lumen. The vessel lumen is for instance healthy or treatment of a local lumen reduction has already been performed by for example a stent placement. In those cases no lesion position is required.

Figure 23:
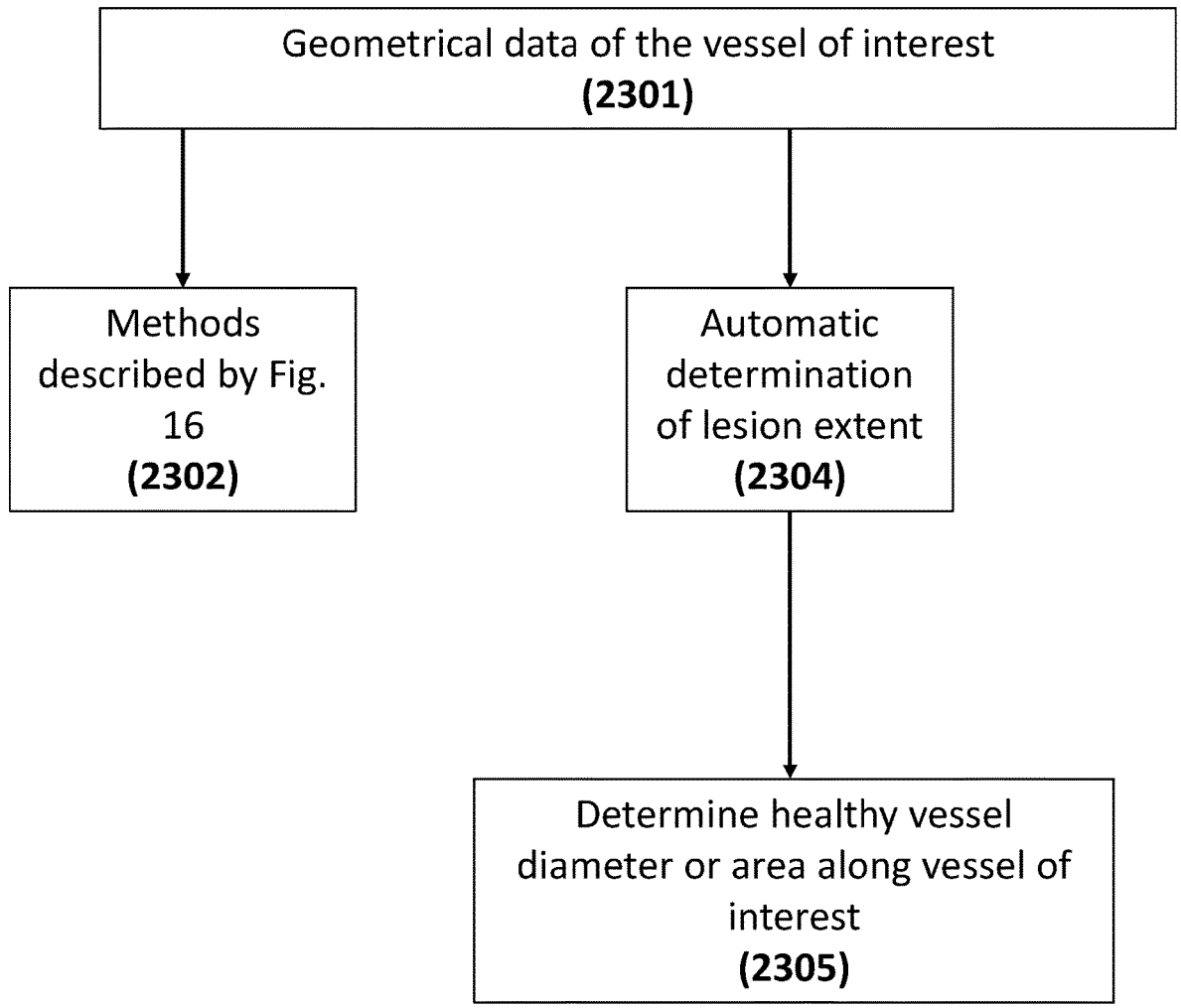
FIG. 23 shows an overview of the different methods to define the healthy reference diameter and/or area graph along the vessel of interest.

Once the lesion position is known an estimation of the healthy reference diameter and/or area graph can be determined. FIG. 23 provides an overview of the different methods to define the healthy reference diameter and/or area graph along the vessel of interest. Represented by step 2301 of FIG. 23 the 3D geometrical data along the vessel of interest is calculated as a result from step 104 of FIG. 1. Based on this geometrical data, two different methods are presented to compute the healthy reference diameter and/or area graph along the vessel of interest. The first method, represented by step 2302, is a collection of the methods as described within this application in relation to FIG. 16. The second method describes an automatic approach represented by step 2304 and 2305. Within step 2304 the lesion extent (length of the lesion) is automatically defined as for instance taught by Gronenschild E, et al. in "*CAAS II: A Second Generation system for Off-Line and On-Line Quantitative Coronary Angiography*", Cardiovascular Diagnosis 1994; 33: 61-75. Next in step 2305 the healthy reference diameter or area graph is computed by for example fitting a line through the diameter or area values along the vessel of interest in which the diameter or area values within the lesion extent are excluded during the fitting as described by Gronenschild E, et al.

Figure 9:
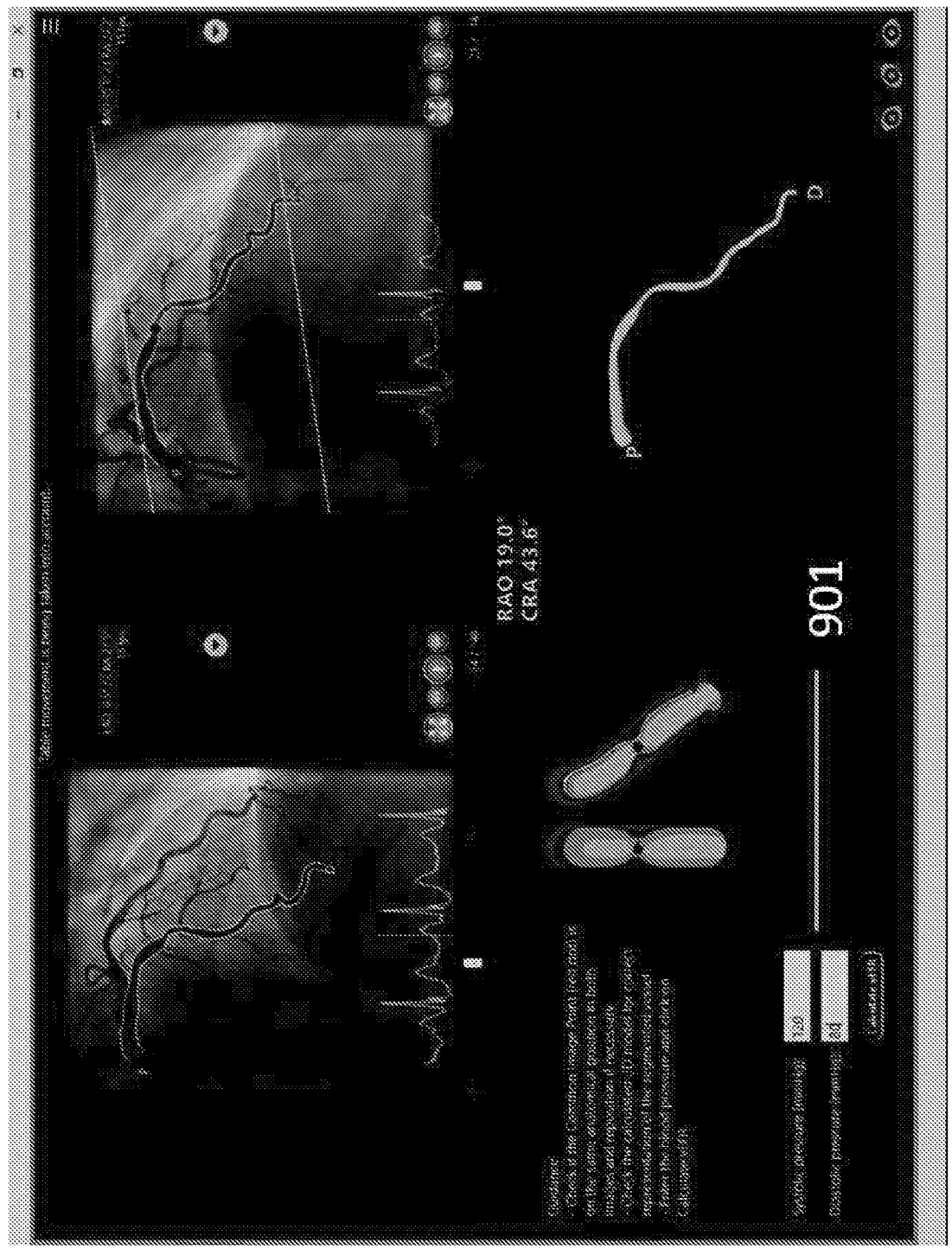
FIG. 9 shows an exemplary workflow screenshot to input patient specific data such as aorta pressure.

Referring back to FIG. 1, patient specific data is used as shown in step 105 of FIG. 1. As described earlier it is an objective of the current application not to add any procedure time. During current PCI interventions it is clinical practice to invasively measure the aortic pressure in rest in a patient for instance using an arterial line. For the vessel FFR calculations it is required that the clinician inputs this pressure as shown in reference 901 of FIG. 9.

In step 106 of FIG. 1 the hemodynamic results are calculated. In order or allow real time computation of the hemodynamic results a low computation method is now disclosed. In summary, the method integrates patient specific aortic pressure as measured during the catheterization procedure. After defining the proximal hyperemic blood flow or blood velocity through the coronary artery, a patient specific velocity is defined by assuming constant healthy velocity within the coronary epicardial system, measured aortic pressure and the 3D geometry of the coronary artery. The detailed description of the method will now be disclosed.

The geometrical information and the patient specific blood pressure are used to calculate the pressure drop for every location along the centerline of the vessel of interest or at a single location. In step 106 of FIG. 1, the vessel FFR value can be derived from the calculated pressure drop. Optionally, a pressure drop and vessel FFR value is calculated for every location along the centerline of the vessel of interest. The latter we refer to as a virtual pull back, which resembles a virtual in-vivo pullback of the calculated pressure drop or vessel FFR values. This virtual pullback provides a tremendous amount of physiological and hemodynamic information of the vessel of interest.

The vessel FFR method is based on the physiology of the coronary circulation. In healthy conditions, coronary blood flow is well adapted to the metabolic needs of the hearth. For instance, during exercise, like running, coronary blood flow increases in response to an increase in myocardium oxygen demand and coronary blood flow is minimum during rest. This principle is called coronary autoregulation and is controlled locally at organ level. The coronary circulation can be conceptually divided into the epicardial conductance vessels and the intramural vessels. Epicardial coronaries covers the coronary arteries with a diameters between 5 mm down to 0.4 mm and are located on the outer surface of the myocardium, and the intramural vessels (diameter <400 µm) are the coronary arteries and arterioles down to the capillary level that comprise the microcirculation. During x-ray angiography, only the epicardial coronary arteries are visualized by the injected contrast liquid. Hemodynamically, blood flow through the vascular system is governed by Ohm's law, which states that flow is equal to the pressure gradient divided by the sum of resistances between the input and output of the vessel. Vascular resistance to blood flow can be described by equation 7, which implies that the resistance is proportional to the vessel length and blood viscosity and inversely proportional to the fourth power of the diameter. This provides the coronary circulation with a powerful mechanism for blood flow regulation by altering smooth muscle tone (e.g., a 30% reduction in vessel diameter results in a fourfold increase in resistance). All coronary arterial vessels with diameters less than 400 µm contribute to flow control, the autoregulation. Dilation of these resistance vessels can increase myocardial blood flow up to meet the increase oxygen demand.

Figure 11:
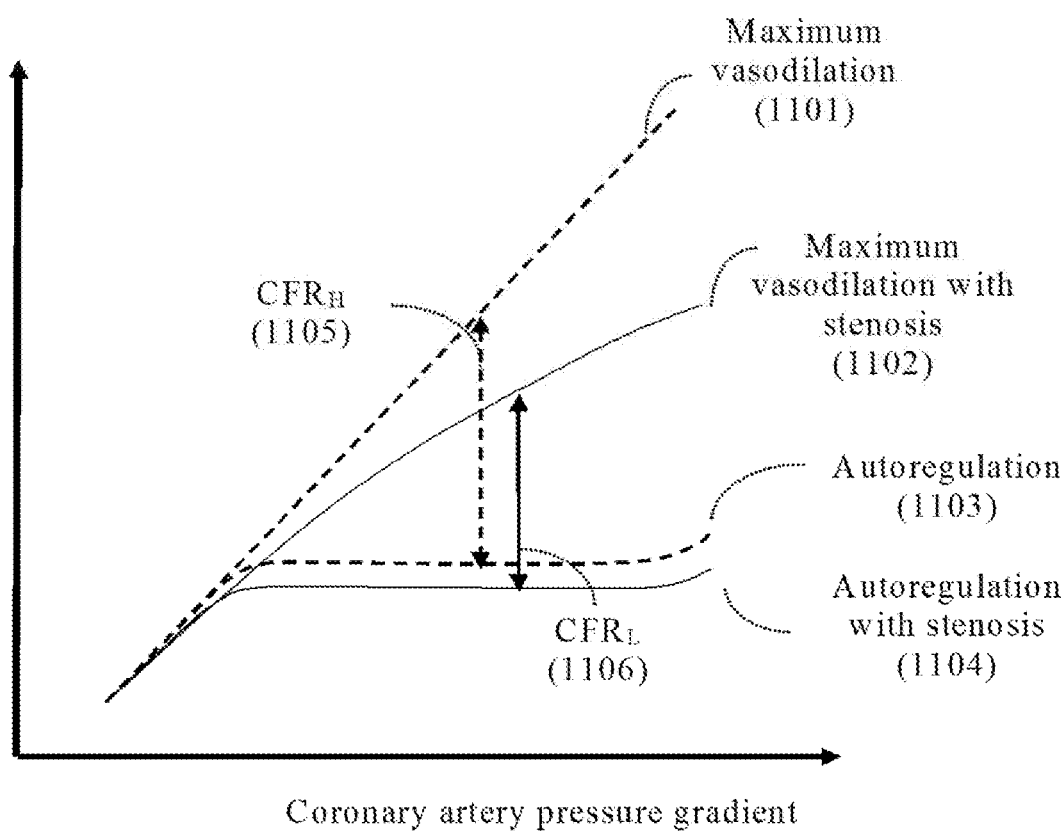
FIG. 11 shows an example of the concept of CFR by means of the relationship between coronary arterial pressure and coronary flow.

In the absence of an epicardial stenosis, maximum flow in humans is reported to rise 4 a 5 times the resting flow in healthy men. This reserve capacity, calculated as the ratio of maximum to resting coronary blood flow, is called coronary flow reserve (CFR). FIG. 11 illustrates the concept of CFR by means of the relationship between coronary arterial pressure and coronary flow. In the presence of vessel tone (dilation of the arterial vessels with diameters less than 400

µm), the pressure flow relationship is characterized by a central flat portion 1103 that represent the autoregulation. The pressure flow relationship at maximum exercise (maximum coronary flow, maximum vasodilation) is a straight line 1101, this is caused by maximum dilation of the microcirculation as a response to maximum vasodilation, resulting that the flow is predominantly a function to the cross-sectional area of the microvascular resistance vessels, which in turn depends on the prevailing distending pressure. A luminal narrowing caused by a stenosis in an epicardial coronary artery represents an additional resistance to blood flow. This resistance can be overcome at rest by compensatory vasodilation, and autoregulated flow only decreases near complete occlusion when the vasodilatory capacity is exhausted (1104). Coronary revascularization is indicated when stenosis severity has reached a level of impaired coronary flow that can no longer meet oxygen demand. This will first be noticeable during exercise. The effect of a stenosis on the coronary pressure—flow relationship at maximal vasodilation is also depicted in FIG. 11 by label 1102, which in this case is characterized by a curvilinear relationship owing to the nonlinear pressure loss induced by the stenosis. This curvilinear relationship is caused by the quadratic relationship between pressure gradient and flow within a stenotic coronary segment. The pressure gradient due to a stenotic segment ($\Delta P$) is the sum of frictional losses, and losses due to convective acceleration and flow separation at the exit of the lesion can be expressed as:

$$\Delta P = fQ + sQ^2, \qquad \text{(equation 1)}$$

where Q represents the coronary flow, and f and s are the viscous and expansions loss coefficients, respectively.

Within FIG. 11, 1105 shows the CFR in a healthy coronary artery at a specific coronary artery pressure. Reference 1106 shows the CFR of coronary artery with a stenosis.

CFR can be measured through a variety of methods, such as Doppler echocardiography and positron emission tomography. During an intervention procedure CFR is measured by intracoronary blood velocity measurements with a Doppler catheter and like invasive FFR, CFR is associated with additional cost and procedure time. Also, in order to induce hyperemia, additional drug infusion is required, which is an extra burden for the patient.

Figure 12:
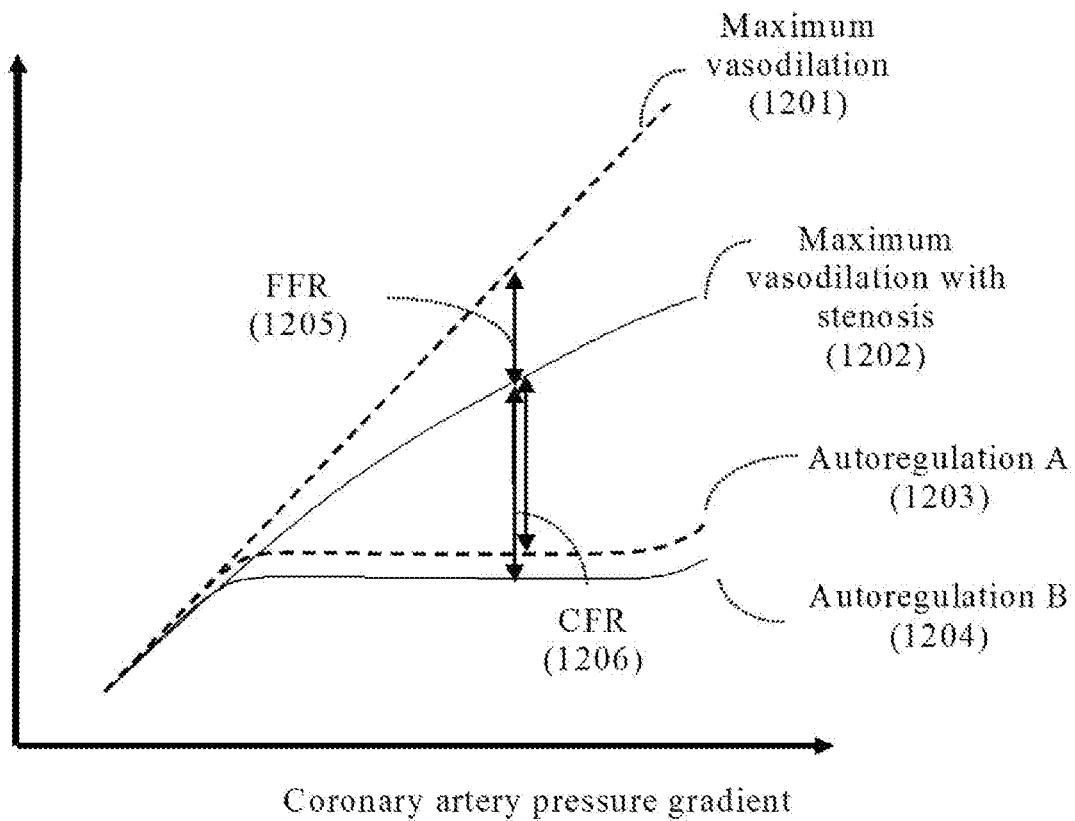
FIG. 12 shows an example of the difference in concept between FFR and CFR.

As mentioned before, CFR is defined as the ratio of maximum coronary blood flow through a coronary artery to its resting coronary blood flow. A disadvantage of CFR is the absence of a unique 'healthy' reference, a reference value is required for each vessel which corresponds to the resting state (FIG. 11, 1103). Due to for instance, patients who suffer from tachycardia, this resting state shift upwards (higher rest flow), resulting in an overestimation of the CFR. Furthermore, within healthy subjects the maximum increase in coronary flow is between 4 a 5 fold related to the resting flow rate, which makes CFR less specific. FFR doesn't suffer from above limitations. As mentioned before FFR is defined as the ratio between the pressure distal to a coronary lesion to the pressure before the coronary lesion (the aortic pressure) as measured during hyperemia. This results that the FFR is an index between 0.0 and 1.0, indicating whether the coronary lesion is functional significant or not by a pre-defined threshold (0.75). Furthermore, FFR is impendent on baseline characteristics (FIG. 11, 1103 or 1104). FIG. 12 shows this difference. 1201 and 1202 represent the coronary pressure—flow relationship at maximal vasodilation for a healthy coronary artery and coronary artery with a lesion. The FFR is represented by 1205 and CFR is represented by 1206. FIG. 12, shows two different CFR values caused by the differences in coronary pressure—flow relationship at rest, in which 1203 represents a patient suffering for instance from tachycardia and 1204 a cases without tachycardia.

Figure 13A:
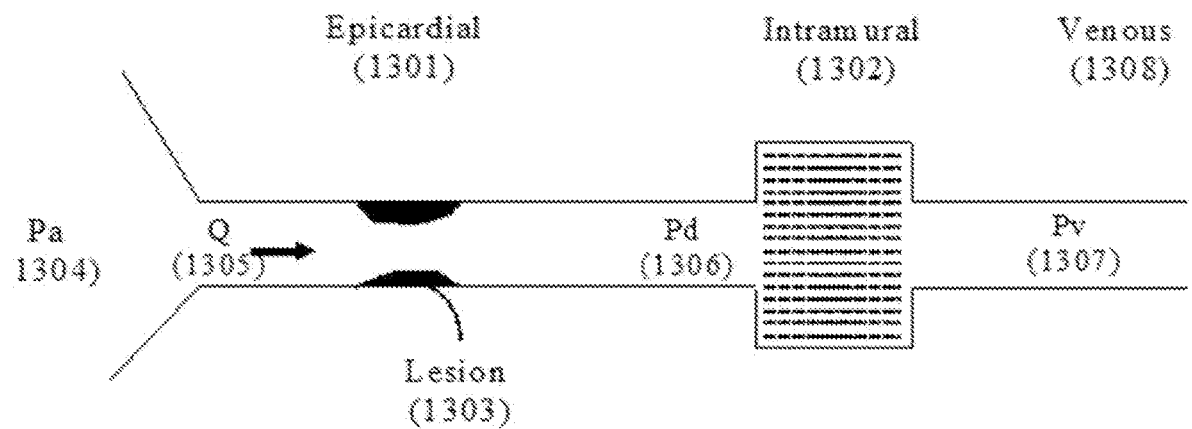
FIG. 13A shows a schematic representation of a coronary lesion in an epicardial coronary artery.

At block 106 of FIG. 1, the hemodynamic results are calculated. In an embodiment of the application an important principle is used to calculate the hemodynamic results. Which is the physical limitation of the maximum pressure drop (gradient) in the coronary system. FIG. 13A shows a schematic representation of the coronary circulation with a coronary lesion 1303 in an epicardial coronary artery 1301. 1302 represent the intramural coronary arteries, also called microcirculation, which connects to the venous system 1308. At each coronary flow 1305, the sum of the pressure drop along a coronary artery ($\Delta P_{cor}=Pa-Pd$; equation 2) and the pressure drop due to the microvasculature ($\Delta P_{micro}=Pd-Pv$; equation 3) can physically not exceed the difference between the aortic pressure 1304 (Pa) and the venous pressure 1307 (Pv). The pressure drop along a coronary artery (FIG. 13B, 1301) is defined as the aortic pressure 1304 (Pa) minus the distal pressure 1306 (Pd) (Pa-Pd). This principle is mathematically described by equation 4 with reference to FIG. 13A as follows:

$$P_a P_v = \Delta P_{cor} + \Delta P_{micro} \qquad \text{(equation 4)}$$

Considering the principle as defined by equation 4, a method is disclosed to quantify hemodynamic parameters, such as pressure drop and FFR comprising the following unique features:

use of 3D coronary geometry information instead of 2D coronary geometry;

computations based on coronary velocity instead of coronary flow; and calculation of patient specific hemodynamic parameters.

Use of 3D Coronary Geometry Information Instead of 2D Coronary Geometry

In an embodiment of the application a method is provided to calculate FFR in which geometry information used is based on 3D QCA is disclosed. The 2D QCA suffers from geometric inaccuracies due to a) out of plane magnifications errors and b) foreshortening errors. Foreshortening is the event when an object seems compressed when viewed from a certain perspective, causing distortion of the geometrical information such as underestimation of length of coronary artery. Since geometric information is an essential part within fluid equations, accurate and reliable coronary geometry information is essential.

Computations Based on Coronary Velocity Instead of Coronary Flow

As mentioned before, CFR is defined as the ratio of maximum coronary blood flow through a coronary artery to its resting coronary blood flow.

However, coronary flow is not straightforward extracted from x-ray angiographic image data and several methods has been developed with variable performance. Furthermore, such methods need specific acquisition requirements, such as a minimum frame rate, an acquisition sequence needs to include image data before and after contrast injection, and the like. As mentioned before vessel FFR needs to fit into the cardiologist's workflow during a percutaneous coronary intervention procedure or during an x-ray coronary angiography procedure and the total analysis time should not add procedure time. Therefore a method is developed which relies on coronary velocity instead of coronary flow.

Figure 18A:
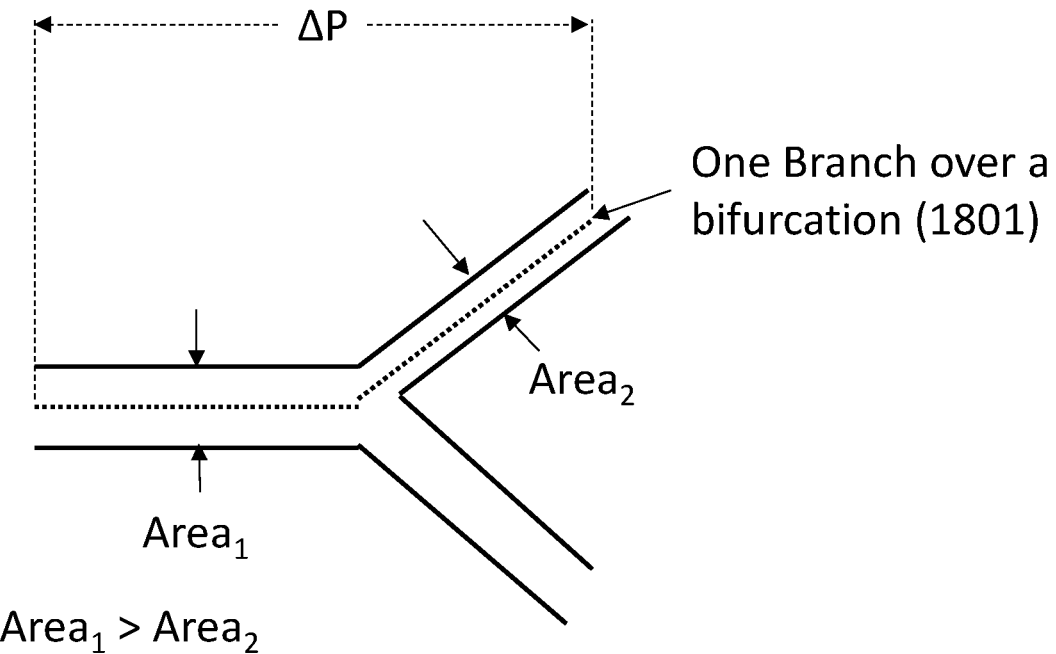
FIG. 18A shows a schematic illustration of a vessel with a bifurcation.
Figure 18B:
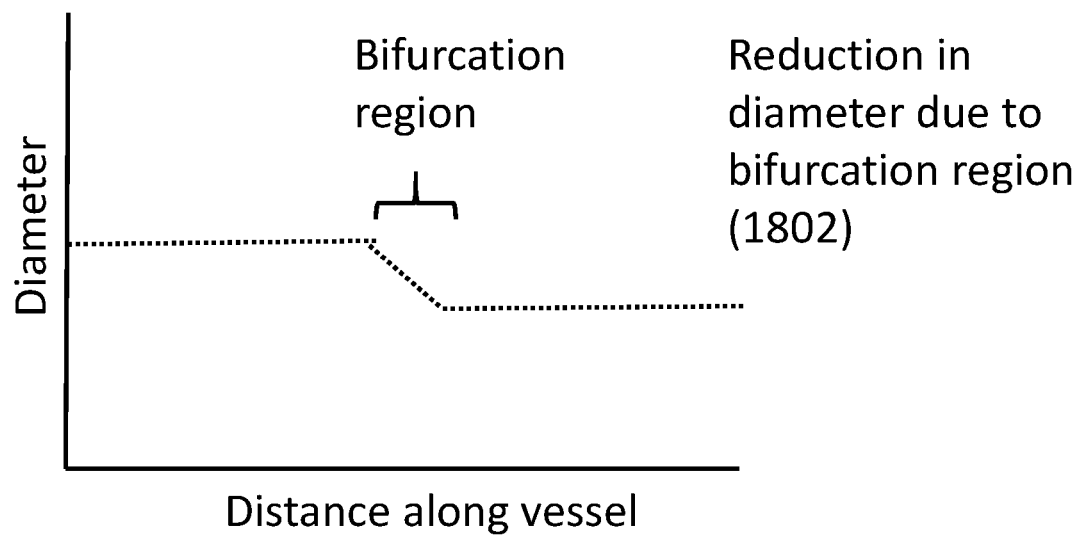
FIG. 18B is a graph showing the diameter along the vessel.

Furthermore, the inventors recognized that coronary velocity has the advantage that coronary velocity is independent of the location within the coronary tree considering a single patient. When analyzing a sub-segment of the coronary tree, the coronary flow through that specific sub-segment depends on the location of that specific sub-segment within the coronary tree, e.g., coronary flow decreases downstream of the coronary tree, this in relation to an approximately constant coronary velocity within the healthy coronary tree. Indeed, the coronary velocity differs between patients, but within a patient coronary velocity is approximately constant. For example, the vessel of interest represents a subset of a coronary tree. The calculations described herein for calculating the hemodynamic results are based in part on an assumption that the coronary tree exhibits a constant velocity throughout. This principle allows to use the proposed embodiment for single vessel, bifurcating or vessels trees. Distal to the bifurcation there is a reduction in the cross sectional area or diameter of the vessel (1802 of FIG. 18B). Therefore the algorithm can be applied over one branch of the bifurcation as illustrated in FIG. 18A (1801) with constant velocity. This means the velocity is assumed constant along the entire vessel tree in healthy situation.

This observation is further used within the description of 'Calculation of patient specific hemodynamic parameters' within current application.

Referring to equation 4 in combination with the use of coronary velocity, the method is further described.

Pressure Gradient $\Delta P_{micro}$ Due to Microcirculation

Referring to FIG. 11, the coronary pressure gradient under maximum vasodilation in a healthy situation (1101) is linear dependent on the flow. In a healthy situation the pressure gradient in the coronary artery is negligible and the linear pressure gradient is caused by the microvasculature. This means that the pressure gradient due to microvasculature, FIG. 13A, Pd (1306) minus Pv (1307) (Pd–Pv), is linearly dependent on the blood flow. At zero coronary flow the pressure gradient caused by the microvasculature is zero and Pd (FIG. 13A, 1306) equals to the venous pressure of the patient (FIG. 13A, 1307). At maximum coronary flow, the pressure gradient is equal to the difference between aortic and venous pressure (FIGS. 13A, 1304 and 1307). This is the case in a fully healthy coronary artery because no pressure gradient is present in the coronary artery itself, and all pressure gradient is observed in the microvascular bed. This can also be expressed in terms of coronary velocity and presented by the dotted line in FIG. 13B, 1316, resulting in equation 5 as follows:

$$\Delta P_{micro} = P_v + \frac{P_a - P_v}{V_{max}} V \quad \text{(equation 5)}$$

The maximum blood velocity $V_{max}$ and Pv (FIG. 13B, 1314, 1307) is an empirically determined value from a large patient population indicating the maximum blood velocity under healthy condition during stress/hyperemia. Alternatively, the maximum blood flow under healthy condition can be empirically determined from a large patient population. The maximum velocity under healthy conditions $V_{max}$ (FIG. 13B, 1314) can be derived from this maximum flow using the inlet area or estimated healthy reference inlet area as described the flowchart of FIG. 23.

Pressure Gradient $\Delta P_{cor}$ Due to Epicardial Coronary Lesion

Referring again to FIG. 13A, the pressure gradient within an epicardial coronary lesion (1303) and defined as Pa (1304) minus Pd (1306) (Pa–Pd), is caused by two main fluid dynamic effects (equation 1) and defined as a friction effect (f) caused by viscous effects and a separation effect (s). Because velocity has the advantage of being independent of location within coronary tree, as explained before, both the friction term f and separation term s can be expressed dependent on coronary velocity using parameters Cv (friction) and Ce (separation) as follows:

$$\Delta P_{cor} = C_v V + C_e V^2 \quad \text{(equation 6)}$$

In accordance with embodiments herein, the formulations dependent on coronary velocity is further explained, having the advantage, as explained before, that velocity is independent of the location within the coronary tree. By utilizing equation 6, the calculations described herein for calculating the hemodynamic results are based in part on an assumption that the coronary tree exhibits a constant velocity throughout.

The friction effect ($C_v$) can be calculated using Poiseuille's law. Because the vessels cross sectional area is not constant along its length (e.g. tapering of vessel) it is more accurate to integrate the Poiseuille's law along the length of the vessel. This friction term depends on blood viscosity and the geometric parameters: e.g. length and vessel radius/area determined from the 3D reconstruction in step 103 of FIG. 1, as follows:

$$C_v = \frac{8 * \mu * L_{tot} * A_{in}}{\pi R^4} \quad \text{(equation 7)}$$

where $\mu$ is a constant representing blood viscosity, and derived from the 3D reconstruction, $L_{tot}$ represents the length of the coronary artery segment, $A_{in}$ represents the proximal area of the coronary artery, and R is the radius of the coronary artery segment.

Because the radius of the coronary artery is not constant along its length, equation 7 can be rewritten by an integral along the vessel length. The advantage of integrating along the entire coronary segment is that the pressure gradient due to friction, which becomes a significant component in small vessels, is taken into consideration.

The separation term ($C_e$) depends mainly on geometric parameters of the coronary obstruction region, as determined in step 103 of FIG. 1. These parameters include the cross sectional area of the stenosis derived from the 3D reconstruction and blood properties such as blood density as follows:

$$C_e = \frac{\rho}{2} * \frac{K_e}{1333} * \left(\frac{A_{in}}{A_{sten}} - 1\right)^2 \quad \text{(equation 8)}$$

where p is a constant representing blood density, $K_e$ contains a term empirically determined from patient data and a dependency to the length of the stenotic segment and normal diameter as derived from the 3D reconstruction, $A_{in}$ represents the proximal area of the coronary artery and $A_{sten}$ represents the area at stenotic segment location as derived from the 3D reconstruction.

In both the $C_v$ and $C_e$ terms the area at inlet of vessel segment ($A_{in}$) is needed. This area can be determined directly from the inlet of the 3D reconstruction. To make it more robust a healthy reconstruction of the vessel of interest can be made using all dimensions of the 3D reconstruction outside the stenosis region (FIG. 23). By using reconstruction of the vessel, the inlet area becomes less sensitive to small segmentation errors. For blood properties such as the density and viscosity of the blood, values from literature can be used. Alternatively, these values are empirically determined value from a large patient population.

Alternatively, instead of using the area at the inlet of vessel segment the healthy area value at the lesion position can be used representing a more specific reference area for the stenosis ($A_{ref}$). $A_{ref}$ can be calculated using the healthy vessel area as determined in FIG. 23. Equation 7 changes to:

$$C_v = \frac{8 * \mu * L_{tot} * A_{ref}}{\pi R^4} \quad \text{(equation 9)}$$

Similar to equation 7, equation 9 can also be rewritten by an integral along the vessel length to take changes in the radius and healthy vessel area of the coronary artery into account. And equation 8 changes into the following formula:

$$C_e = \frac{\rho}{2} * \frac{K_e}{1333} * \left(\frac{A_{ref}}{A_{sten}} - 1\right)^2 \quad \text{(equation 10)}$$

Figure 24:
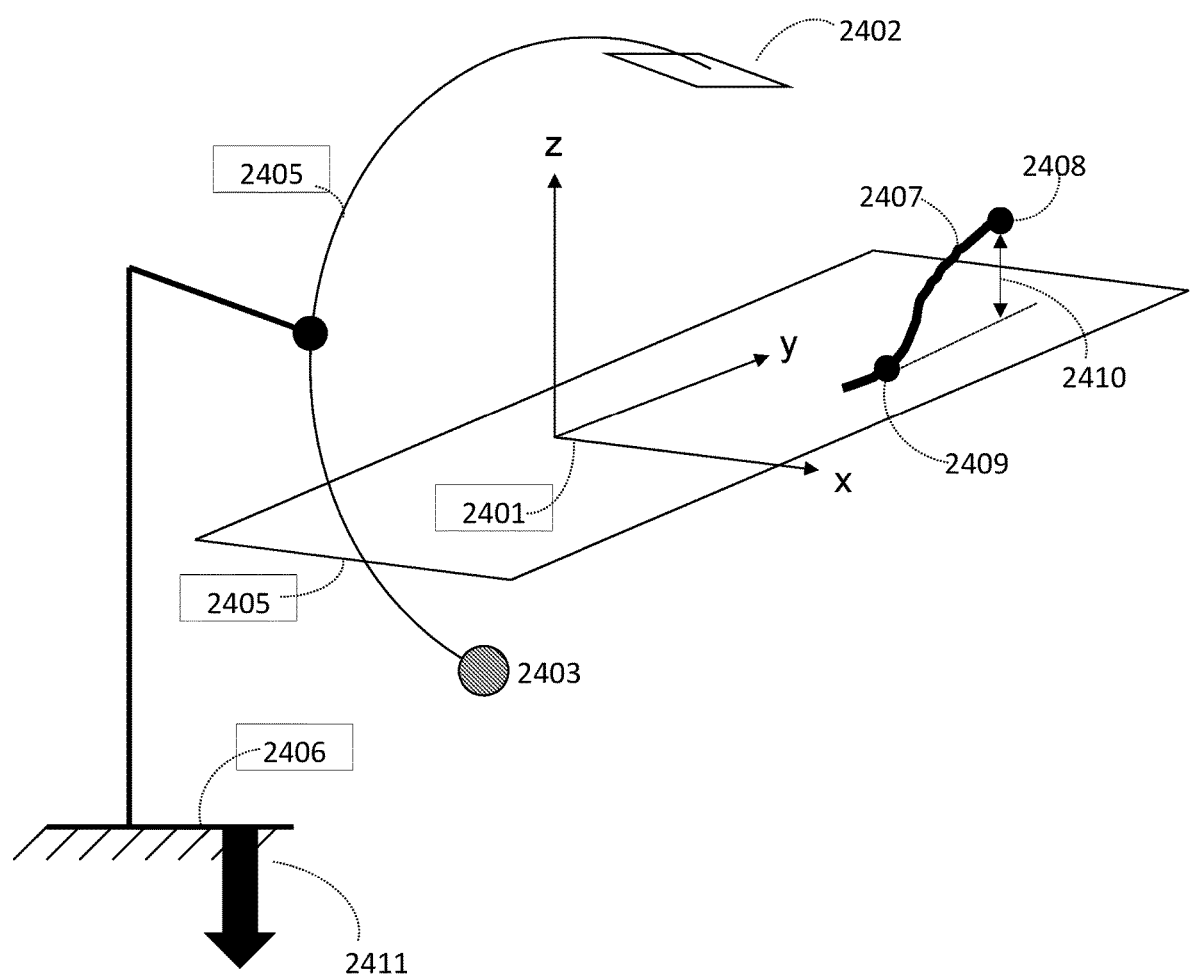
FIG. 24 illustrates the correlation of the coordinates system of the 3D reconstruction of the vessel of interest to the physical world coordinate system.

Additionally, in case there is a height difference in the vertical or 'up' direction (altitude different) between the proximal and distal pressure measurement point, hydrostatic pressure should be taken into account. The 3D reconstruction of the vessel reveals the altitude difference along the vessel centerline between the proximal side and the distal side of the vessel. FIG. 24 illustrates the correlation of the coordinates system of the 3D reconstruction of the vessel of interest, as a result from step 102 of FIG. 1, to the physical world coordinate system (e.g. relative to the imaging system). A schematic illustration of the imaging system (e.g. X-ray system) is represented by image intensifier (2402), X-ray source (2403), c-arm (2404) and table on which the patient is positioned (2405). The coordinate system is illustrated by 2401, in which the z-axis is defined perpendicular to the ground (2406) (e.g. surface of the earth) and the x-axis and y-axis are defined orthogonal to the z-axis. An altitude difference (or elevation) along the vessel of interest is defined by the difference in the z-component of the 3D coordinate. Within FIG. 24 two location along the 3D reconstruction are visualized and represented by 2409 and 2410. For instance, to compute the elevation (2410) between two locations (2408 and 2409) of the 3D reconstruction (2407), the altitude difference is computed by 2409.z minus 2408.z (2409.z-2408.z). The altitude difference causes a pressure gradient due the gravitational forces (2411 of FIG. 24) acting on the blood. The gravitational pressure gradient ($\Delta P_g$) is added to equation 6 and results in the following equation:

$$\Delta P_{cor} = C_v V + C_e V^2 + \Delta P_g \quad \text{(equation 11)}$$

The availability of this height/gravitation information is also an advantage of using a 3D reconstruction based on multiple x-ray projections instead of the usage of a single 2-dimensional projection. The pressure gradient due to gravitational forces along the vessel of interest can be calculated using equation 12:

$$\Delta P_g = \rho g \Delta h \quad \text{(equation 12)}$$

where ρ represents the density of blood, g represents the gravitational acceleration and Δh is the difference in altitude of the proximal and distal vessel part (e.g. 2410 of FIG. 24).

Optionally, the gravitational acceleration can be adjusted according to its specific value depending on the location on the earth surface.

Calculation of Patient Specific Hemodynamic Parameters

Figure 13B:
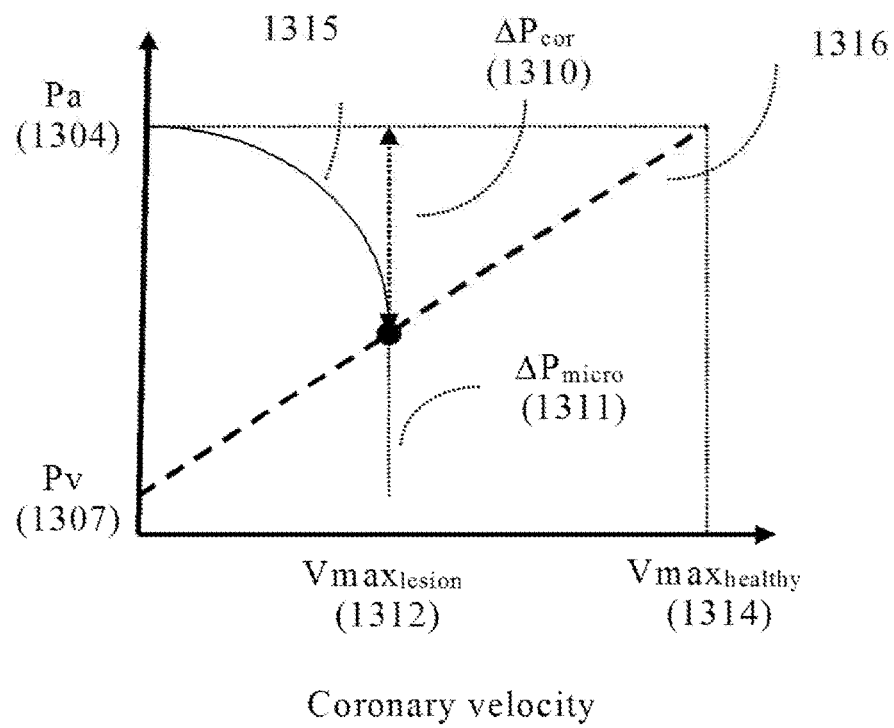
FIG. 13B shows the coronary vessel pressure relationship adopted from the pressure flow relationship of CFR.

FIG. 13B shows the relationship between coronary velocity and coronary pressure with the knowledge incorporated from equation 4 and pressure flow relationship. Within FIG. 13B, the x-axis represents the coronary velocity and the y-axis represents the coronary pressure at location 1306 of FIG. 13A. As mentioned during the description of 'Pressure gradient $\Delta P_{micro}$ due to microcirculation', 1316 represents the pressure gradient observed in the microvascular bed (FIG. 13A, 1302) in the case that the epicardial coronary is healthy. This relationship is linear with the increase of coronary velocity. The maximum coronary velocity 1314, reflects the velocity during maximum exercise when assuming that the epicardial coronary is healthy. The sum of venous pressure (Pv 1307) and pressure gradient due to microcirculation ($\Delta P_{micro}$ 1311) at maximum coronary velocity (FIG. 13B, 1314) needs to be equal to aortic pressure 1304 (Pa). Since maximum vasodilation results in an increased flow at equal coronary artery pressure (FIG. 12, FIG. 13), the patient specific aortic pressure at rest can be used. This patient specific aortic pressure is preferably derived from the measured end-diastolic and end-systolic pressure using the guiding catheter. The guiding catheter is placed in the coronary ostium and the aortic pressure is measured by connecting a transducer. From the measured aortic pressure trace, the end-diastolic and end-systolic pressure can be obtained. Vessel FFR uses the mean aortic pressure. The mean aortic pressure is calculated, for instance a weighted average of both end-diastolic and end-systolic pressure. Alternatively, the patient specific aorta pressure can be measured at the brachial artery using a pressure cuff measurement. Within FIG. 13B, 1315 represent the pressure distal to an epicardial coronary lesion (FIG. 13A, 1306), and as mentioned during the description of 'Pressure gradient $\Delta P_{cor}$ due to epicardial coronary lesion', this curve has a parabolic shape. The more severe the coronary obstruction (FIG. 13A, 1303), the faster this curves goes down with increase coronary velocity. Next, by incorporating equation 4, the maximum velocity (hyperemic) within this specific patient can be defined by the intersection of curve 1316 with 1315. Within the example of FIG. 13B, this maximum velocity is represented by 1312, $\Delta P_{cor}$ by 1310 and $\Delta P_{micro}$ by 1311.

With this information, hemodynamic parameters, such as FFR (vessel FFR) can be computed. The vessel FFR value is the fraction of coronary pressure distal of a coronary lesion (1303) divided by the aortic pressure. The distal pressure can be calculated by subtracting pressure drop (1310) from the aortic pressure (1304) as follows:

$$\text{vessel } FFR = \frac{P_d}{P_a} = \frac{P_a - \Delta P_{cor}}{P_a} \quad \text{(equation 13)}$$

An illustrative embodiment and the according workflow and methods are described above. Next, alternative embodiments which include alternative and/or optional workflows and/or methods are described.

In embodiments, the luminal boundaries are detected (step 403 and 407 of FIG. 4) in the select frame (step 402 and 406 of FIG. 4). Optionally, multiple image frames over time of the same image sequence (401 of FIG. 4) are used to improve the luminal boundary detection. The number of additional image frames is variable, and can include one or more image frames available in the image sequence. The use of additional image frames over time has added value to the luminal boundary detection algorithms. The additional image frames can be used to improve the image quality or to incorporate more information about the vessel geometry and/or the total coronary tree geometry in the boundary detection algorithms.

Figure 19:
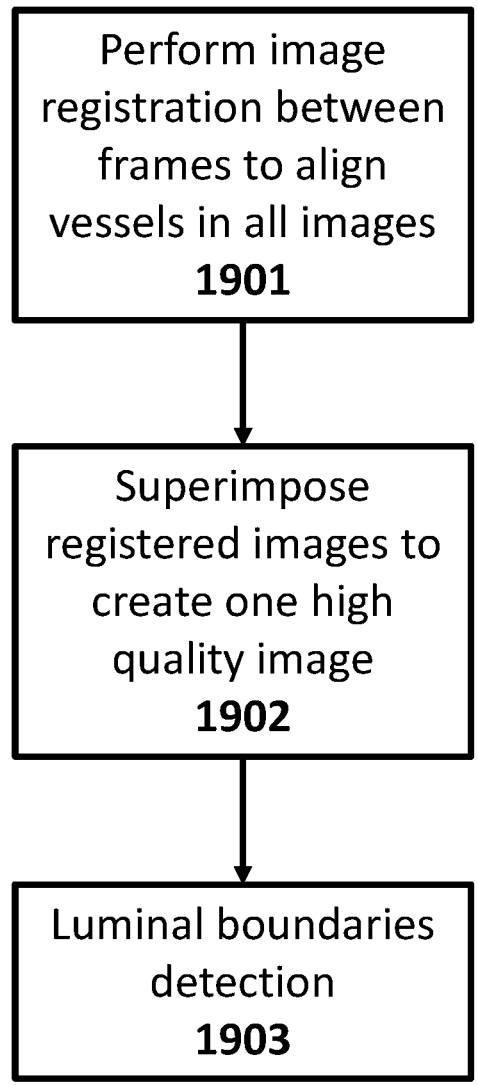
FIG. 19 shows a flow chart of a method for improving luminal boundaries detection using image registration of multiple image frames.

Image quality improvement can be achieved by aligning the image frames using image registration techniques (1901 of FIG. 19). Image registration can be done for example as thought by for example Fischer et al., "*Non-rigid image registration*", In: http://www.mic.uni-luebeck.de/uploads/tx_wapublications/2006-KOREA-BF.pdf, 2006. After alignment of the image frames, the image frames are superimposed onto each other by step 1902 of FIG. 19 to improve the image quality. Next, in step 1903 of FIG. 19, the luminal borders are detected in the superimposed image.

Furthermore, using multiple image frames of the image sequence adds temporal information about the 3D orientation and/or geometry of the vessels of interest and other vessel(s) present in the image sequence. The temporal information can be used for example to make a better distinction between bifurcations and crossing and/or overlapping vessels. For instance bifurcation side branches will have similar motion behavior while crossing and/or overlapping vessels move independently from each other. Using multiple image frames might reveal parts, or details of the vessel of interest that were invisible in some image frames but are clearly visible in other image frames due to the motion of the vessels. The use of the additional image frames increases the probability of a good projection/visibility of the vessel details and will contribute to improve the luminal border detection. Alternatively, a rotation angiography image sequence can improve the luminal border detection. Because a rotation angiography varies the viewing angle over time overlapping vessels within one viewing angle will become visible in other viewing angles. The ECG signal can be used to match the cardiac phase between viewing angles.

Optionally, more than one stenotic segment can be included in the calculation of coronary pressure gradient (equation 6), by adding multiple Ce terms (equation 8) representing the specific stenotic segment.

Optionally, no stenotic segment can be present, in this case the term Ce is removed from equation 6.

In step 104 of FIG. 1, the lesion position is determined based on the 3D geometry of the vessel segment. Besides this, more innovative functional parameters can be used for the lesion position determination. These functional parameters are for example related to fluid mechanics. The functional parameter may also be referred to as a flow pattern parameter as the parameter is indicative of select flow characteristics at one or more points along a vessel of interest. The Reynolds number is an example of such a functional fluid mechanics parameter. The Reynolds number is an important dimensionless quantity in fluid mechanics used to predict flow patterns in fluid. At low Reynolds numbers, flows tend to be dominated by laminar flow, while at high Reynolds numbers flows tend to be dominated by turbulence results from differences in the fluid's speed and direction. The Reynolds number indicates the presence of turbulence and can be used to indicate the presence of a lesion in case the Reynolds number exceeds a fixed threshold or dynamic threshold value based on for example the vessel morphology. An example in which the vessel morphology is used to define a dynamic threshold is by including variations in vessel morphology, like for instance the vessels tortuosity, curvature or local vessel dilatations such as aneurysm.

In accordance with embodiments herein, the flow pattern parameter may be a Reynolds number, wherein embodiments calculate a series of Reynolds numbers at a series of corresponding points along a length of the vessel of interest. The lesion position can be based on changes in the Reynolds number. For example, the Reynolds numbers may be compared to one another to identify relative changes between them. For example, evaluating Reynold numbers along the vessel segment of interest by comparing its minimum and maximum values. Optionally, one or more Reynolds number may be compared to a threshold that defines a cut-off between a laminar flow pattern and a turbulent flow pattern. As a further example, a ratio or difference between Reynolds numbers may be utilized to evaluate vessel morphology and the estimated healthy situation (e.g., see FIG. 23). In accordance with the foregoing, the determining operation at step 104 of FIG. 1 is based, at least in part, on calculation of a flow pattern parameter indicative of whether flow is laminar or turbulent. For example, the flow pattern parameter is a Reynolds number.

Another example to determine the lesion position is by identifying variations in blood velocity along the vessel caused by the presence of vessel narrowing. Within present application the velocity is assumed constant in healthy vessels along the coronary tree. Due to vessel narrowing the blood velocity increase at the lesion and decreases again at lesion outlet due to the widening of the vessel to its constant velocity ($V_{constant}$). The local velocity ($V_{local}$) can be calculated using the local healthy estimated area (Area) and local vessel area ($A_{local}$) using equation 14 as follows:

$$V_{local} = \frac{A_{ref}}{A_{local}} \cdot V_{constant} \qquad \text{(equation 14)}$$

A fast decrease in blood velocity, which can occur at the lesion outlet due vessel widening, can cause flow turbulence. Identification of locations of fast blood velocity changes can be done by for example, the ratio or the difference between the local healthy velocity ($V_{constant}$) and the local diseased velocity ($V_{local}$). Another example is change/ratio in local velocity between lesion and distal to the lesion.

Next to this, the lesion position can be determined by including for example 1-dimensional wave propagation and/or use of computational fluid dynamics (CFD) as taught in the art by Shi et al., "*Review of Zero-D and 1-D Models of Blood Flow in the cardiovascular System*", BioMedical Engineering OnLine (2011) 10:33, and/or simplified mathematical approaches like equation 1. CFD simulations of entire coronary vessels are time consuming, therefore, to reduce computation time and resource candidate regions (2006 of FIG. 20) of the vessel (tree) are identified in which 1-dimensional wave propagation or CFD is applied. Identification of these regions can be based for example on vessel morphology, for example regions of the vessel (tree) that differ from the assumed healthy reference (FIG. 23) Another method to identify candidate lesion regions is to include the parts of the vessel that shows a local decrease in diameter or area.

Figure 20:
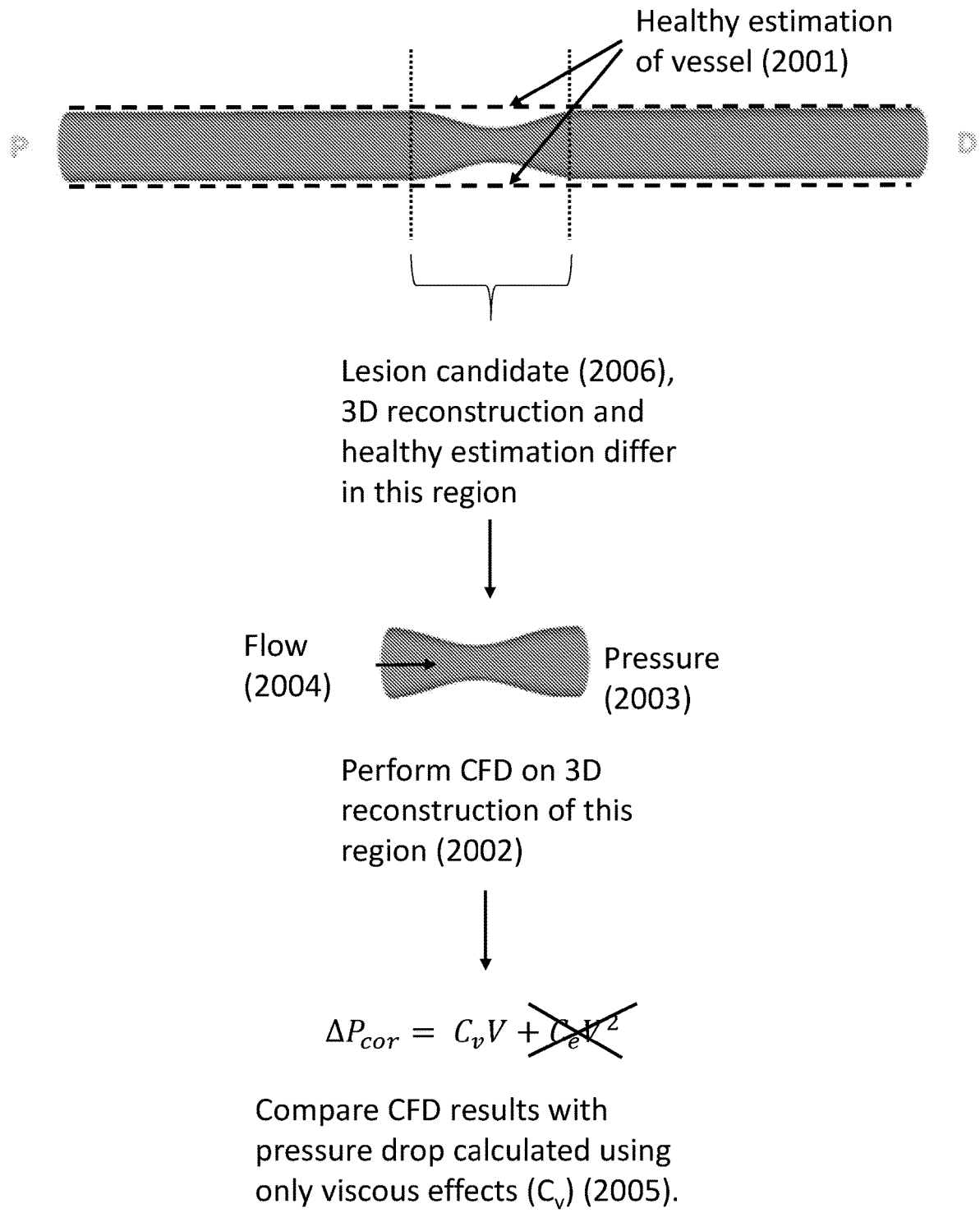
FIG. 20 shows an exemplary workflow to identify lesion positions using CFD.

In 2002 of FIG. 20, CFD is applied to the candidate regions. CFD calculations require boundary conditions at the inlet (2004) and at the outlet (2003). At the inlet a flow value is set and at the outlet a stress free outlet is applied as taught in the art by for instance (Wentzel, et al., 2005). For the inlet boundary condition, flow or velocity is applied (2004 of FIG. 20) which can be determined empirically from a patient population or can be estimated using the method as describe in the section 'Calculation of patient specific hemodynamic parameters' with the difference that the calculation of $\Delta P_{cor}$ (equation 6) is done by neglecting the separation term ($C_e$) (the separation term is the only term that depends on the lesion location). At the outlet boundary, a zero pressure boundary condition (2003 of FIG. 20) is applied. In case the pressure drop as calculated by 1-Dimensional wave propagation or by CFD does not match the pressure drop as calculated by using equation 6 in which the separation term ($C_e$) is neglected (2005 of FIG. 20), a lesion must be present.

Alternatively, other derived terms from CFD can be used to identify a lesion. For example flow separation, turbulent kinetic energy, vorticity are parameters which describes flow behavior. At the lesion exit flow separation can occur resulting in energy loss, therefore, flow separation is an indication of the presence of a lesion. Turbulent kinetic energy provides information about the energy loss caused by turbulence. Because a lesion can cause turbulence it is a parameter that can identify the presence of a lesion. Vorticity is also a measure related to the exit of a lesion. Vortexes can be created at flow separation regions and therefore indicating the presence of a lesion.

Next to this, machine learning can be used to determine lesion position(s). The machine learning method can identify lesions based on the morphology of the vessel (tree). Optionally this can be combined with estimated healthy vessel 3D morphology which can be determined as thought in U.S. Pat. No. 7,155,046 entitled "Method of Determining Physical Parameters of Bodily Structures" issued to Aben et al.

Optionally, 2D image intensities of the coronary vessel of interest can be incorporated in machine learning approaches, providing information about through plane vessel dimensions. Alternatively, changes in image intensities due to X-ray absorption of contrast liquids can be used in the machine learning approach.

Furthermore, additional patient specific characteristics, like aortic pressure, age, weight, patient length, clinical history of the patient can be incorporated in machine learning approaches providing information about probability of lesion presence.

Figure 14:
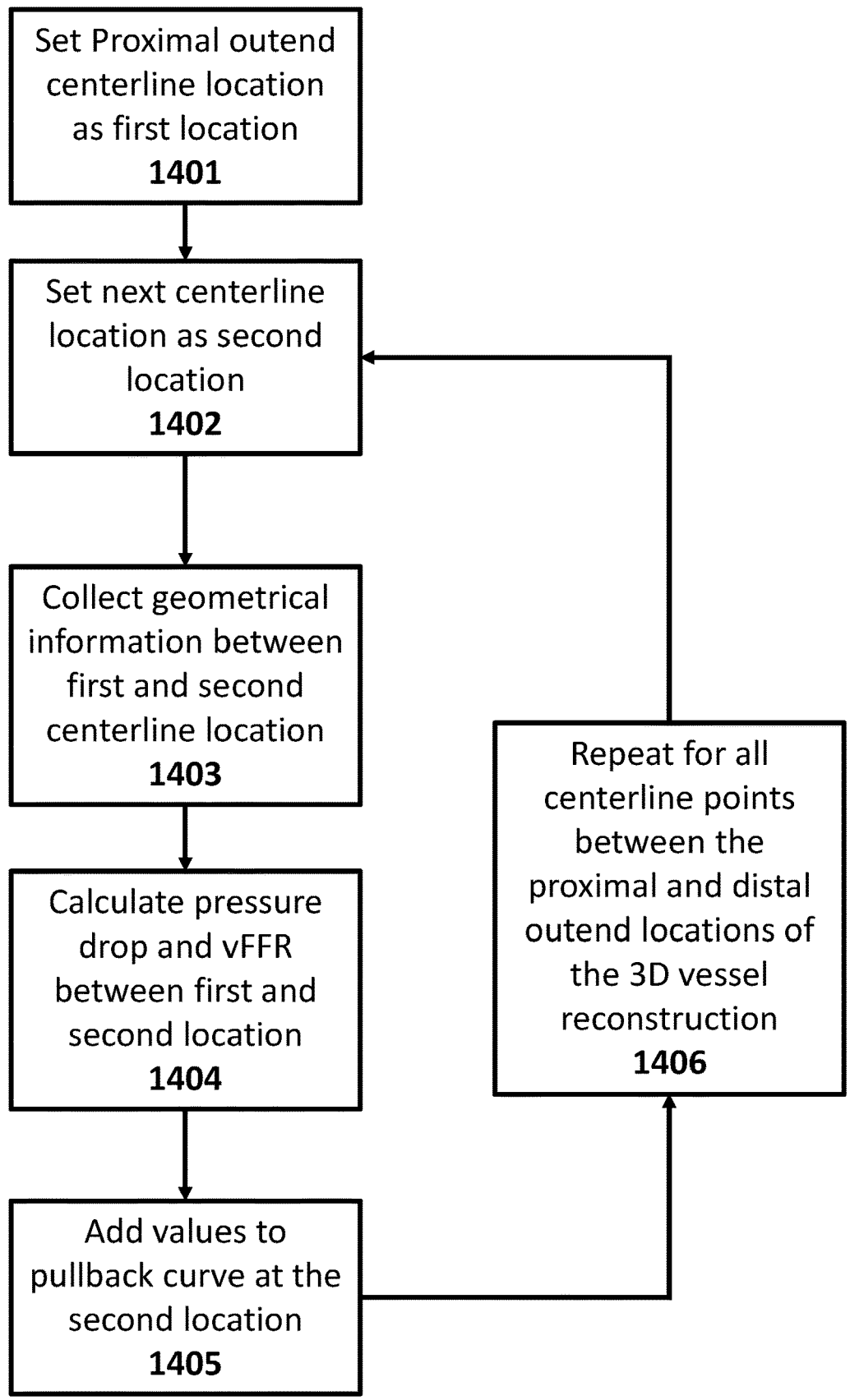
FIG. 14 shows a flow chart of a method for performing a virtual pullback.

Optionally, a virtual pullback of the pressure drop along the centerline of the vessel of interest is calculated. FIG. 14 shows a schematic diagram showing aspect of the method for generating a virtual pullback.

Figure 15:
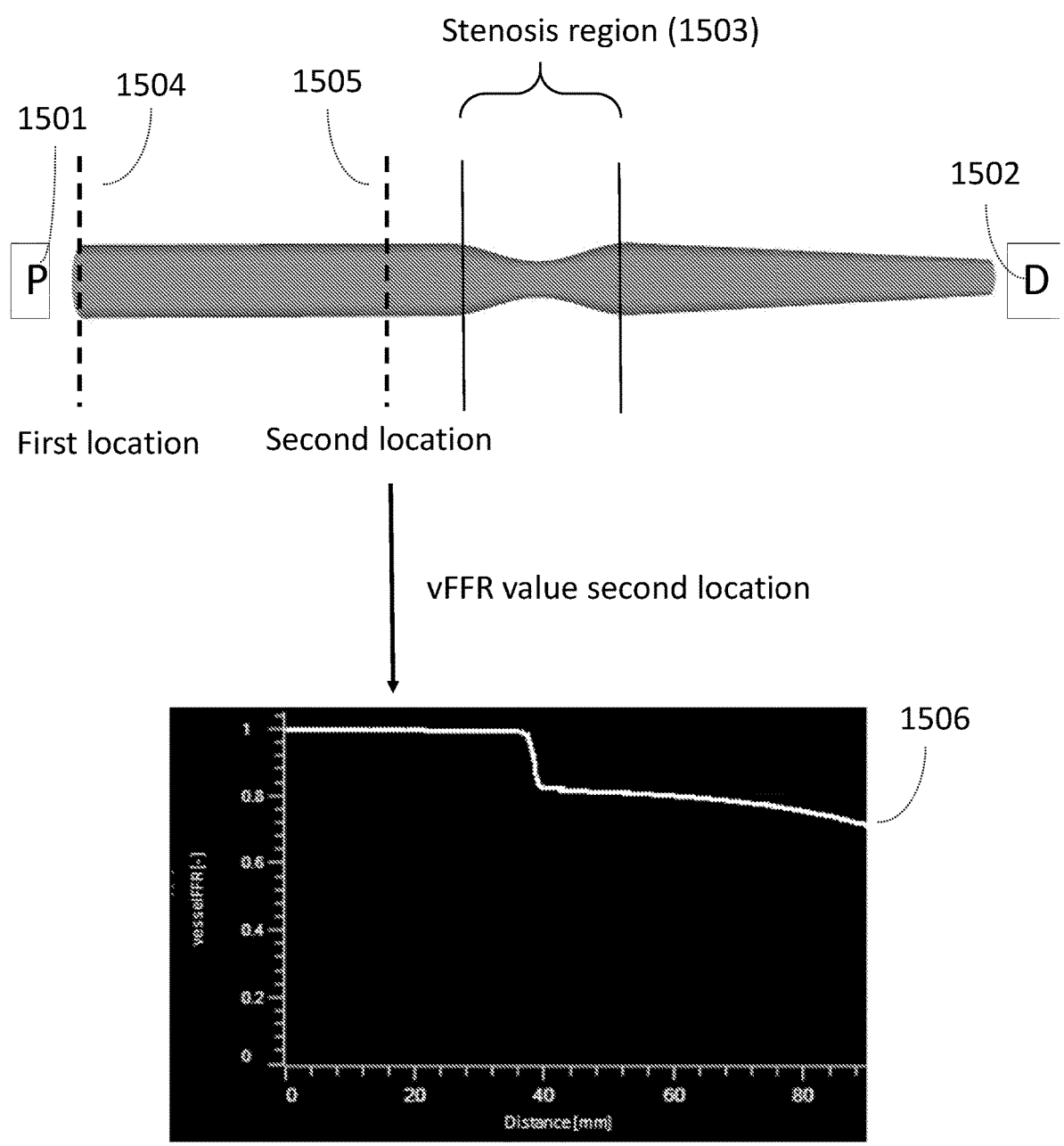
FIG. 15 shows an example of a coronary vessel in which pressure drop in the vessel in also caused by tapering of the vessel.

The 3D reconstruction of the vessel of interest includes a 3D centerline. This 3D centerline comprises a number of centerline points. The first centerline point corresponds with the start location of the 3D reconstructed vessel of interest, and is called proximal (FIG. 15, 1501). The last centerline point corresponds with the end location of the 3D reconstructed vessel of interest, and is called distal (FIG. 15, 1502). All other centerline points represent a location between the proximal and the distal endpoint of the 3D reconstructed vessel of interest. For every centerline point the local geometrical information of the 3D reconstructed vessel of interest is available.

Calculation of the virtual pullback starts at the proximal end of the 3D reconstruction of the vessel of interest. In step 1401 of FIG. 14, the proximal centerline point is set as the first location (FIG. 15, 1504) and remains the first location during the complete virtual pullback calculation.

The centerline line of the 3D reconstructed vessel of interest consist of a number of centerline points as described before. Starting with the next centerline point after the first location, in step 1402 of FIG. 14 this point is set as the second location.

In step 1403 of FIG. 14, the geometrical information from the 3D reconstruction of the vessel of interest corresponding to the segment between the first and second locations are collected.

Using the geometrical information of the segment between the first and second location, the pressure drop and vessel FFR value at the second location with respect to the first calculation are calculated in step 1404 in FIG. 14, using the previously described equations.

Once the pressure drop and vessel FFR value are calculated between the first and second location, the pressure drop and vessel FFR value are added to the pullback curve data corresponding the second location position in step 1405 in FIG. 14.

After the calculated pressure drop and vessel FFR value at the second location is added to the virtual pullback curve, the second location is updated and set to next centerline point location. Referring to step 1406 in FIG. 14, the process is repeated for all centerline points between the first location and the distal end position of the 3D reconstruction of the vessel of interest. After the last centerline point has been processed and the pressure drop and vessel FFR value are added to the virtual pullback curve, the virtual pullback curve is ready.

The virtual pullback is calculated iteratively along the 3D centerline by moving the second location from the proximal side to distal side of the 3D reconstructed. Referring to FIG. 15, the second location (1505) is proximal to the stenosis region (1503). In the vessel part proximal to the stenosis region, the separation term $C_e$ in equation 6 can be neglected and only the viscous effects are present.

Alternatively, the virtual pullback curve can be generated by setting the first location (FIG. 15. 1504) at a different location than the proximal end of the 3D reconstruction of the vessel of interest (FIG. 15, 1501). The first location may be set for example to the proximal lesion border position.

Alternatively, the virtual pullback curve can be generated by finishing before the distal end of the 3D reconstruction of the vessel of interest (FIG. 15, 1502). The final second location of the virtual pullback calculation may be for example the distal obstruction border.

Alternatively, the virtual pullback curve (FIG. 15. 1606) can be calculated from the distal end to the proximal end of the 3D reconstruction of the vessel of interest. In this approach the first location corresponds to the distal end of the 3D reconstruction, which is equal to the last centerline point of the 3D centerline. The first location remains the same for the whole pullback calculation. The second location corresponds with the previous centerline point of the 3D centerline. For every, centerline point a pressure drop and vessel FFR value is calculated between the first and second location. For the calculation of the pressure drop and vessel FFR between the first and second location, the geometrical information of the vessel segment between the first and second location is collected from the 3D reconstruction of the vessel of interest. Once, the pressure drop and vessel FFR value are calculated between the first and second location the pressure drop and vessel FFR value are added to the pullback curve data at the second location position. The process is repeated for all centerline points between the first location and the proximal end position of the 3D reconstruction of the vessel of interest, where the proximal end of the 3D reconstruction of the vessel of interest corresponds with the centerline point at the start of the 3D centerline.

As can be seen in FIG. 15, the distal vessel FFR value is not fully accounted by the stenosis region but is also ascribed to the fact that the diameter of the distal vessel decreases, so called tapering. In vessels with smaller diameters, the friction term $C_v$ (Poiseuille's law) of the above calculations becomes more apparent therefore increasing the pressure drop and decreasing the vessel FFR value.

The virtual pullback information provides added value to the clinical measured distal FFR value only. The virtual pullback provides in detail the hemodynamic impact of the local vessel geometry. The virtual pullback supports the clinician in decision making. The virtual pullback can for example be used to determine if a vessel has a focal or diffuse lesion based on the shape of the virtual pullback. A virtual pullback curve is illustrated in FIG. 15. Focal lesions are local obstructions that can be treated by dilating the stenosis using balloon that can be inflated possibly followed by placing a Stent or scaffold. Diffuse lesions require different treatment approaches and need to be distinguished from focal lesions to prevent unnecessary costs, patient risks and patient comfort by non-optimal treatment decisions.

In an embodiment, the process identifies a treatment segment based on the lesion position. For example, the treatment segment may at least partially overlap the lesion position. Optionally, the treatment segment may be located at a position separate from the lesion position.

Figure 28A:
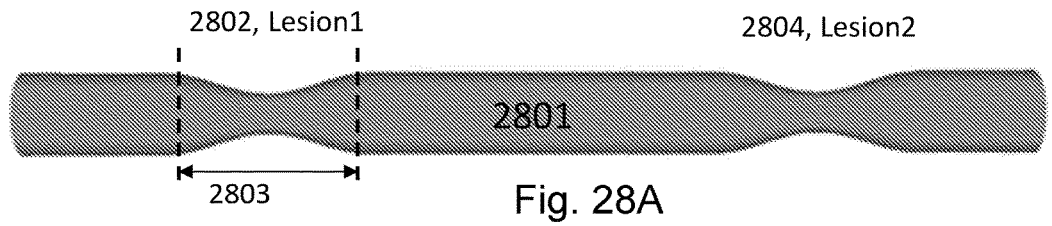
FIGS. 28A-28D are schematic illustrations of the operations that predict pressure loss reduction, or the vessel FFR, by eliminating a lesion segment.
Figure 28B:
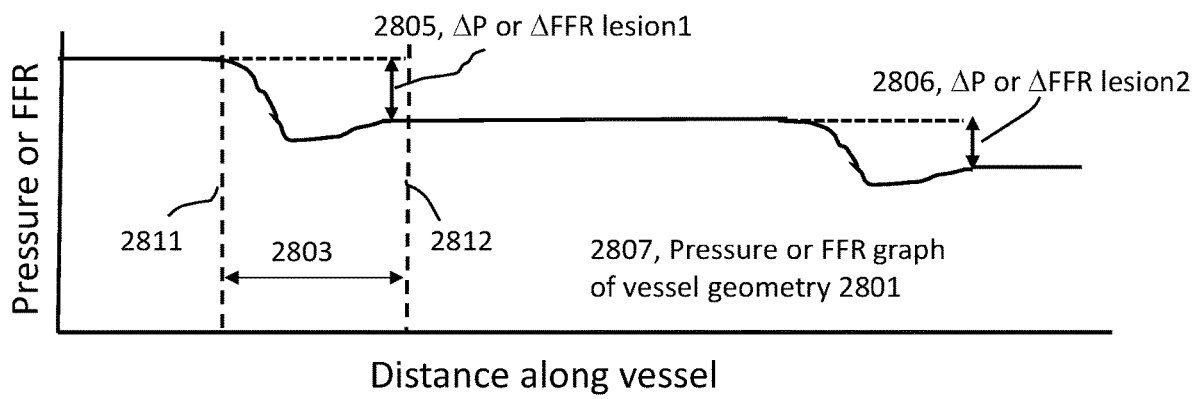
Figure 28C:
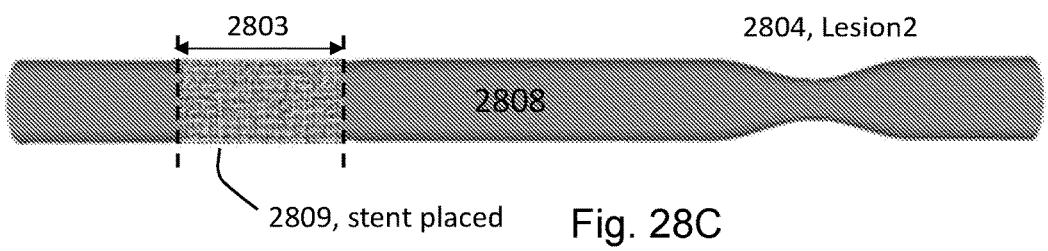
Figure 28D:
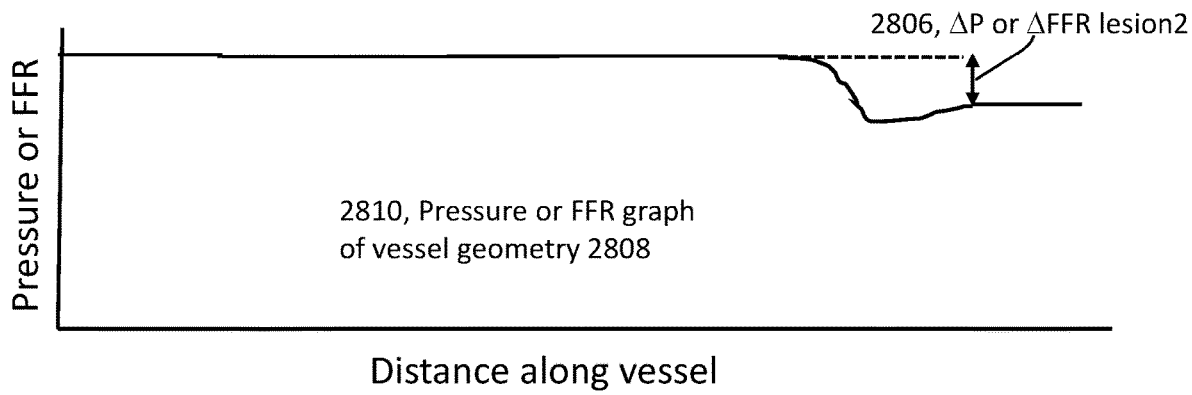

More evidence is found in literature as described in Pijls et al., "*Coronary Pressure Measurement After Stenting Predicts Adverse Events at Follow-Up*" circulation 2002:105: 2950-2954, that after the intervention, such as stent placement or balloon angioplasty, additional (invasive) FFR measurements must be performed to verify that the intervention results in a hemodynamically healthy vessel. This is caused by the effect that after treatment of a lesion, the total resistance of the vessel will decrease resulting in an increase of the blood flow. An increased blood flow will give rise to an increase blood velocity. In case the vessel of interest of interest shows multiple lesions (for instance as illustrated by 2801 of FIG. 28A), this increase in the blood flow will increase the pressure drop over remaining untreated lesion(s) or possible diffuse narrowing of the vessel.

It is understood that the term "remove" as used to describe a lesion is not limited to treatments that physically remove the lesion from a body. Instead, when a lesion is treated, such as by placement of a stent, balloon angioplasty or other treatment method, the lesion is considered to be "removed" as the treatment has displaced the plaque or other blockage material at least partially from the normal flow path through a segment of a vessel. A lesion is considered to be "removed" when the treatment accomplishes a goal of the surgical procedure. It is also recognized that a lesion is considered to be removed, even if the treatment only partially restores a vessel to its healthy area or diameter. For example, when a treatment increases flow by a desired percentage (e.g., 20% or more), the treatment is considered to "remove" the plaque or other blockage material.

A straightforward method to predict the pressure loss reduction, or the vessel FFR, would be to eliminate the pressure loss caused by the lesion that will be treated by for instance a stent placement or balloon angioplasty as illustrated by FIGS. 28A-28D. Within FIGS. 28A-28D, 2801 represent a coronary vessel with two lesions, 2802 lesion 1 and 2804 represent lesion 2. A virtual pull back graph, representing the FFR along the coronary vessel or a virtual pressure loss graph of the vessel 2801 is indicated by 2807. Within this graph, the delta pressure loss or delta FFR are indicate by 2805 for lesion 1 and 2806 for lesion 2. Assuming lesion 1 is to be treated by stent placement with a stent length of 2803, the resulting coronary geometry is illustrated by 2808, in which 2809 illustrates the stent placed with 2803 as stent length. The virtual pull back graph or virtual pressure loss graph resulting from the treated coronary artery 2808 is presented by 2810. Within this graph (2810) the pressure loss or FFR caused by the region (or lesion segment) identified by 2803 of graph 2807 (lesion 1, 2802) has been removed. This is performed by extrapolating of the FFR or pressure from the proximal location of lesion 1 (2811) to the distal location of lesion 1 (2812) and shift the remaining of the graph in y-direction to the extrapolated value at position 2812. The downside of this approach is that the principle explained in section "Calculation of patient specific hemodynamic parameters" within current application is not applied on the treated vessel. Resulting in incorrect pressure drops of untreated lesions. Furthermore the friction effect of region 2803 is neglected, which can be considerable depending on the length and diameter of this region.

Figure 29A:
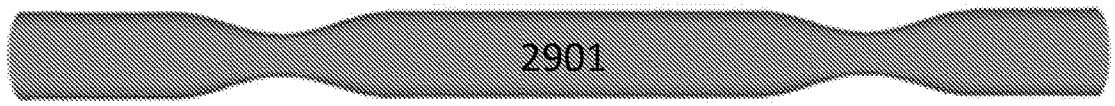
FIGS. 29A-29C are schematic illustrations of the operations that predict pressure loss reduction, or the vessel FFR, by incorporating the healthy vessel estimation.
Figure 29B:
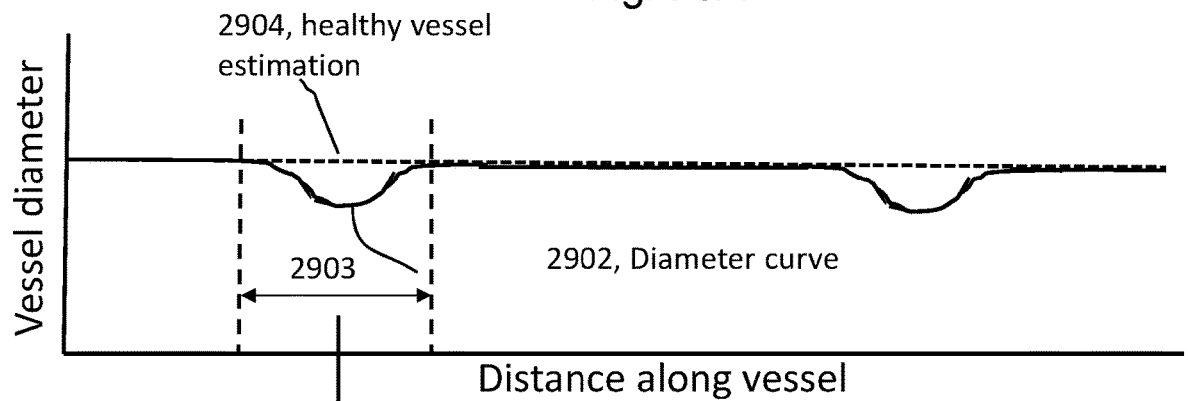
Figure 29C:
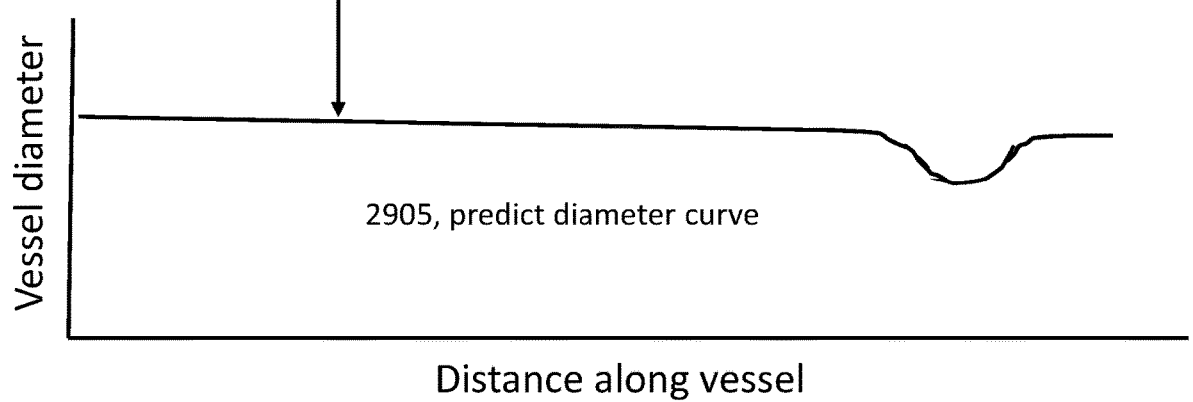
Figure 30:
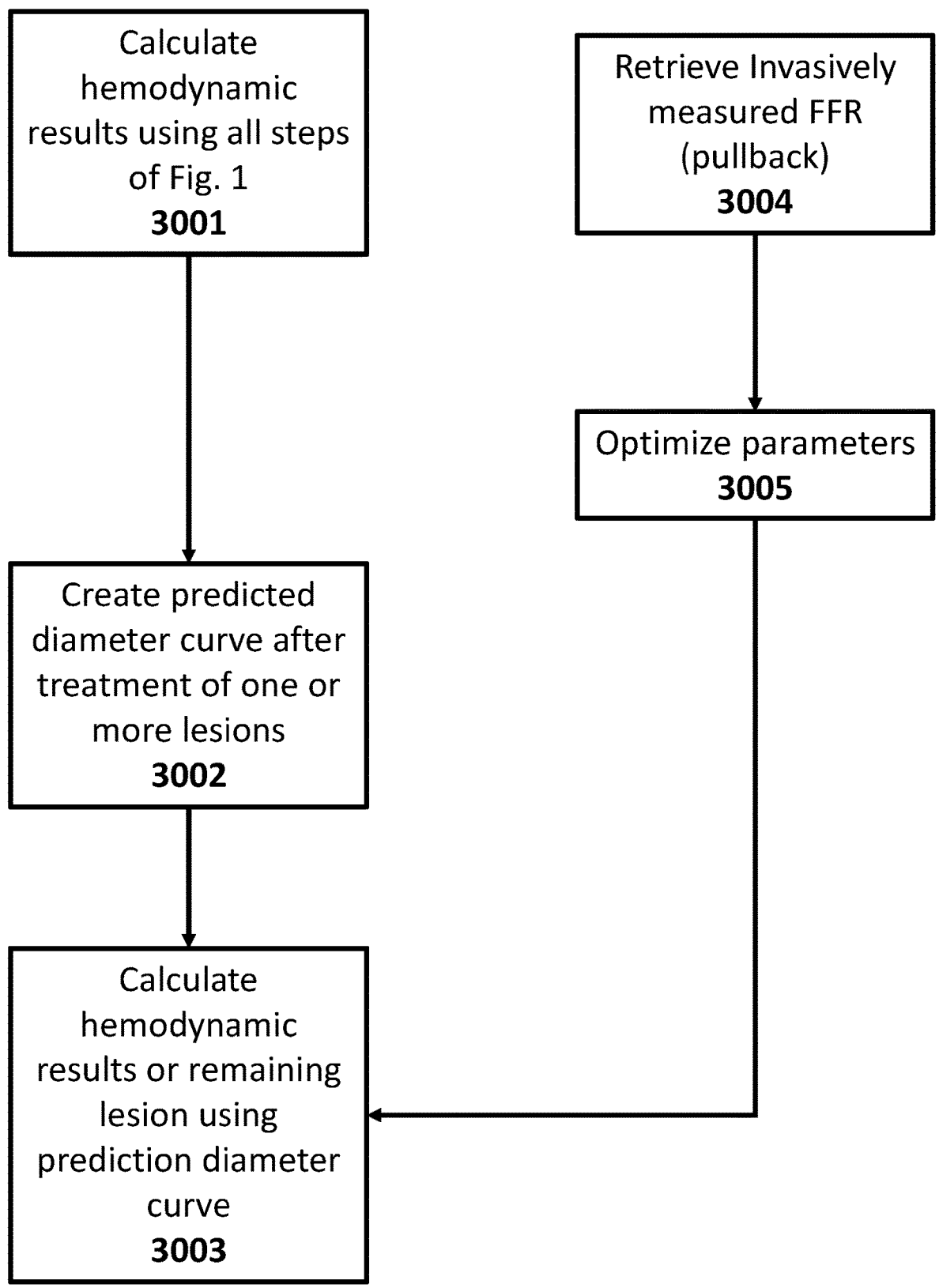
FIG. 30 shows a flow chart of a method for the prediction of treatment.

To incorporate the method as described before in section 'Calculation of patient specific hemodynamic parameters' within current application for the prediction of treatment, the healthy vessel estimation 2904 of FIGS. 29A-29C is used. FIG. 30 shows a flow chart of a method for prediction of FFR after treatment by use of the healthy vessel estimation. This approach does not require any modification of the 3D reconstruction of the vessel of interest, and can be applied fast without or very limited user interaction, by automatically replacing part(s) of the diameter curve by values of the healthy estimated diameter curve. Furthermore, the approach provided in the flow chart of FIG. 30 avoids repeating of the workflow of FIG. 1 or invasive FFR measurements after clinical treatment.

Within step 3001, the hemodynamic results of the untreated vessel of interest, for instance as illustrated by 2901 of FIG. 29A-29C or 2801 of FIGS. 28A-28D, is performed and is identical to the flow chart presented by FIG. 1.

Within step 3002 of FIG. 30, the diameter or area graph of the vessel of interest resulting from step 103 of FIG. 1 is adjusted to reflect treatment of one or more lesions identified by the clinician and is further described with reference to FIGS. 29A-29C. Within FIG. 29A-29C, 2901 illustrates a coronary vessel with two lesions. The diameter curve (or area) (2902) is visualized as derived by step 103 of FIG. 1 and is based on the 3D reconstruction of the vessel as performed by step 102 of FIG. 1. After the identification of the lesion segment to be treated by the clinician (2903), a healthy diameter or area is computed (2904) which corresponds to the healthy vessel dimension (either diameter or area) and is derived by one of the methods as described by FIG. 23. Next, a prediction of the diameter curve is performed by incorporating the healthy vessel estimation within the lesion segment (2904) into the diameter curve 2902 resulting in a predicated diameter or area curve 2905.

Within step 3003, the predicated diameter curve (2905 of FIG. 29C) is used to calculate the significance of a vessel/lesion(s) after treatment and the method is identical to step 106 of FIG. 1.

Optionally, the effect of friction on the blood due to the material of the stent can be taken into account by equation 6, 7, 9 and/or 11. For example this can be achieved by incorporating an additional friction or energy loss term within the equations.

Figure 21A:
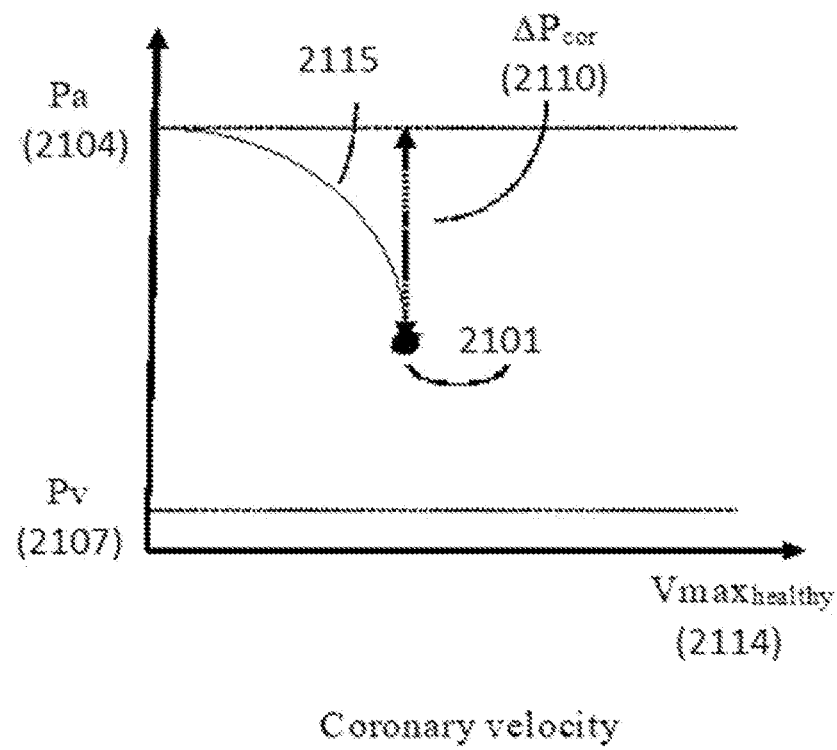
FIGS. 21A and 21B are schematic illustrations of the operations that define the maximum healthy velocity.
Figure 21B:
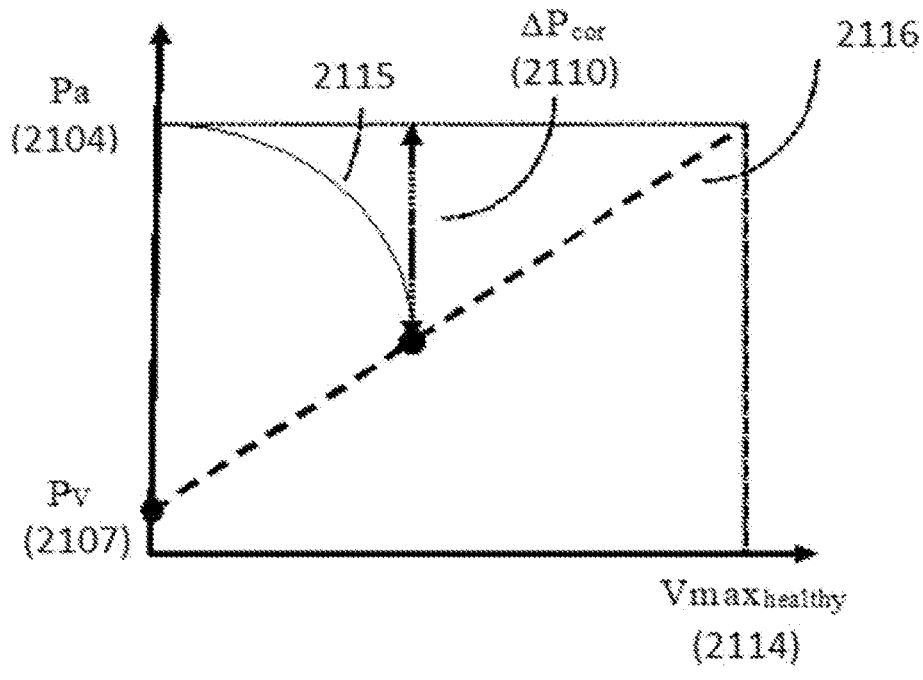

Optionally within step 3004, invasive FFR measurement are retrieved to determine more patient specifically parameters which are used in the equations. In case the invasive FFR measurement is performed by an invasive pullback FFR, the most distal FFR measurement can be used in step 3005. For example, the maximum healthy velocity 1314 of FIGS. 13A and 13B can be determined as illustrated in FIGS. 21A and 21B. The shape of curve 2115 is derived from the vessel geometry, as a result from step 103 and step 104 of FIG. 1, (equation 6 or 11) and $\Delta P_{cor}$ (2110) is known from the invasive measurement. The point 2101 at which curve 2115 equals $\Delta P_{cor}$ (2110) can now be determined. The line representing the $\Delta P_{micro}$ (2116) as function of velocity can now be calculated as a linear line from $P_v$ (2107) trough point 2101. The velocity at which the line (2116) reaches the measured aortic pressure, as a result from step 105 in FIG. 1 ($P_a$, 2104), identifies the maximum velocity (hyperemic) in case of healthy vessel(s) for this patient $V_{max\ healthy}$ 2114, which corresponds to 1314 of FIG. 13 and Vmax of equation 5. This patient specific maximum healthy velocity has the advantage that it incorporates for example possible microvascular diseases. Using the patient specific maximum healthy velocity (2114), enables for instance to a better estimation of the virtual pullback calculations along the vessel of interest (as described by the flowchart of FIG. 14), and supports in providing of improved insights in treatment strategy. Furthermore, in case of serial lesions (tandem lesion), the more patient specific parameters (result of step 3005) and the predicted treatment diameter curve resulting from step 3002, can be used to determine the significance of the remaining lesion(s) by step 3003. Advantage of this embodiment is that no additional invasive measurements are needed to assess the significance of the remaining lesion(s) after treatment of one or more lesions, reducing costs and patient discomfort from adenosine.

Figure 22:
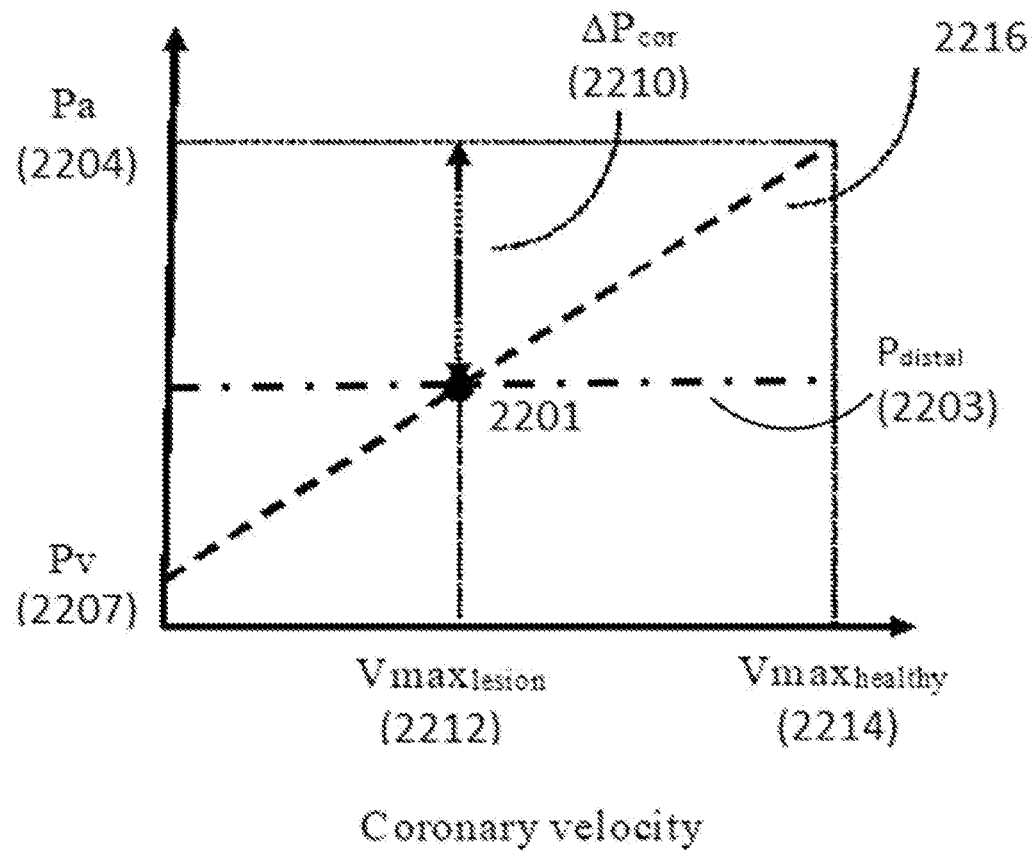
FIG. 22 is a schematic illustration of the operations that define maximum velocity in a vessel segment.

Alternatively, in case the invasive FFR measurement is performed by an invasive pullback FFR, the parameter $C_e$ can be determined patient specifically for each lesion. By using invasive measured pressure values for each lesion. This can be an invasive measured pressure or FFR distal and or proximal to the lesion. First the maximum velocity of the diseased vessel (2212 of FIG. 22) can be determined. This can be done by calculating $P_{distal}$ (2203 FIG. 22) by subtracting the pressure drop due to the lesion(s) ($\Delta P_{cor}$ 2210) from the aortic pressure ($P_a$ 2204). The intersection of $P_{distal}$ (2203) with line 2216 gives the maximum velocity (2212). In serial lesions equation 6 can be rewritten as:

$$\Delta P_{cor} = \Sigma_{i=1}^{n} C_v(i) \cdot V + \Sigma_{i=1}^{n} C_e(i) \cdot V^2 \qquad \text{(equation 15)}$$

where n is the total number of lesions, $\Delta P_{cor}$ is known from invasive measurement, constant V equals 2212, and $C_v$ is calculated for each lesion according to equation 7.

For every lesion an unknown $C_e$ value remains, these n unknown $C_e$ values can be determined using n invasive measurements distal and or proximal to each lesion and makes the method of this embodiment more accurate for treatment prediction. These determined more patient specific parameters can now be used to determine the significance of the remaining lesion(s) by step 3003 using the predicted treatment diameter curve resulting from step 3002. Advantage of this embodiment is that no additional invasive measurements are needed to test the significance of the remaining lesion(s) after treatment of other lesions, reducing costs and patient discomfort from adenosine.

Alternatively, in case serial lesions have a small distance between each other, hemodynamic interaction between the stenosis can effect pressure drops and FFR value, also called cross-talk in literature (Sezer M. et al., "*New Mathematical Correction Model in Pursuit of Optimal Hemodynamic Assessment of Serial Coronary Artery Disease: Overcoming Hyperemic Cross Talk Between Coronary Stenoses in Series*," J Am Heart Association 2018 Oct. 16; 7(20): e010754. doi: 10.1161/JAHA.118.010754). Invasive FFR can be used to identify presence of possible interaction and determine additional parameter(s) to incorporate cross-talk in the calculations. In case invasive FFR pullback differs from the virtual pullback might be an indication for the presence of cross-talk and lesion interaction terms can be added to equation 6. Lesion interaction terms can be for example parameters or terms that increase or decrease pressure drops of lesions.

Calculation of patient specific hemodynamic parameters can be extended/improved by estimating information about blood flow/velocity using image information. Methods to determine the blood velocity/flow as described by EP3403582 "Method and apparatus for determining blood velocity in X-ray angiography images" can be used as is to improve the patient specific hyperemic blood velocity (1312 of FIG. 13B) determined in section "Calculation of patient specific hemodynamic parameters". For example, the maximum blood velocity (1312 of FIG. 13B) determined in section "Calculation of patient specific hemodynamic parameters" can be replaced by the blood velocity determined using image information or a weighted average velocity of both methods can be calculated and used for further calculations.

Equation 5 assumes that the microvasculature is healthy. However, in case of microvascular disease or reduced function of the myocardium its resistance to the blood is increased. The status of the myocardium microvasculature can be determined by the processor by performing myocardial blush calculations and incorporated in equation 5. Myocardial blush is for instance calculated using two-dimensional angiographic images. In a frame of an angiographic image run a region of interest is defined distal to the expected infarct area. A motion correction between the frames in the image run is calculated using for instance correlation technique. The region of interest is shifted per frame according to the calculated motion offset. A background mask is composed in every frame of the image run by for instance a median filter. The average pixel intensity in the region of interest per image mask (e.g. 5 by 5 pixels) is calculated by subtracting the calculated background mask to image intensity of the original image for all images in the image run. In this way only image intensity of small sized structures are taken into account over time. In this way the myocardial blush can be quantified over time within the region of interest. The myocardial blush calculations as known in the art, as taught, for instance, by Vogelzang et al. "*Computer-assisted myocardial blush quantification after percutaneous coronary angioplasty for acute myocardial infarction: a substudy from the TAPAS trial*", European Heart Journal (2009) 30, 594-599. This can be done for one or multiple large or small sections of the heart.

Because the calculations are performed on two-dimensional angiographic images, the section of the heart that the user wishes to investigate suffers from foreshortening and superimposing. However in order to accurately determine the myocardium status, these effects is preferably minimized.

This can, for instance, be done by performing a 3D blush measurement. That is, by performing a blush measurement in both projection used to construct the 3D reconstruction or any other bi-dimensional projection. In each image the user indicates a region in which the measurements should be performed. Using the geometric information belonging to both image perspectives, for example rotation, angulation, magnification, an intersection region of the images can be calculated. Using this information, a distinction can be made between, for example, the posterior side or anterior side of the myocardium.

Optionally, in case an invasive FFR measurement is performed and there is a mismatch between the invasively measured FFR and vessel FFR this is an indication of microvascular disease. In case of this indication of microvascular disease myocardial blush calculations can be performed and provide more insights in presence of microvascular disease.

Figure 17:
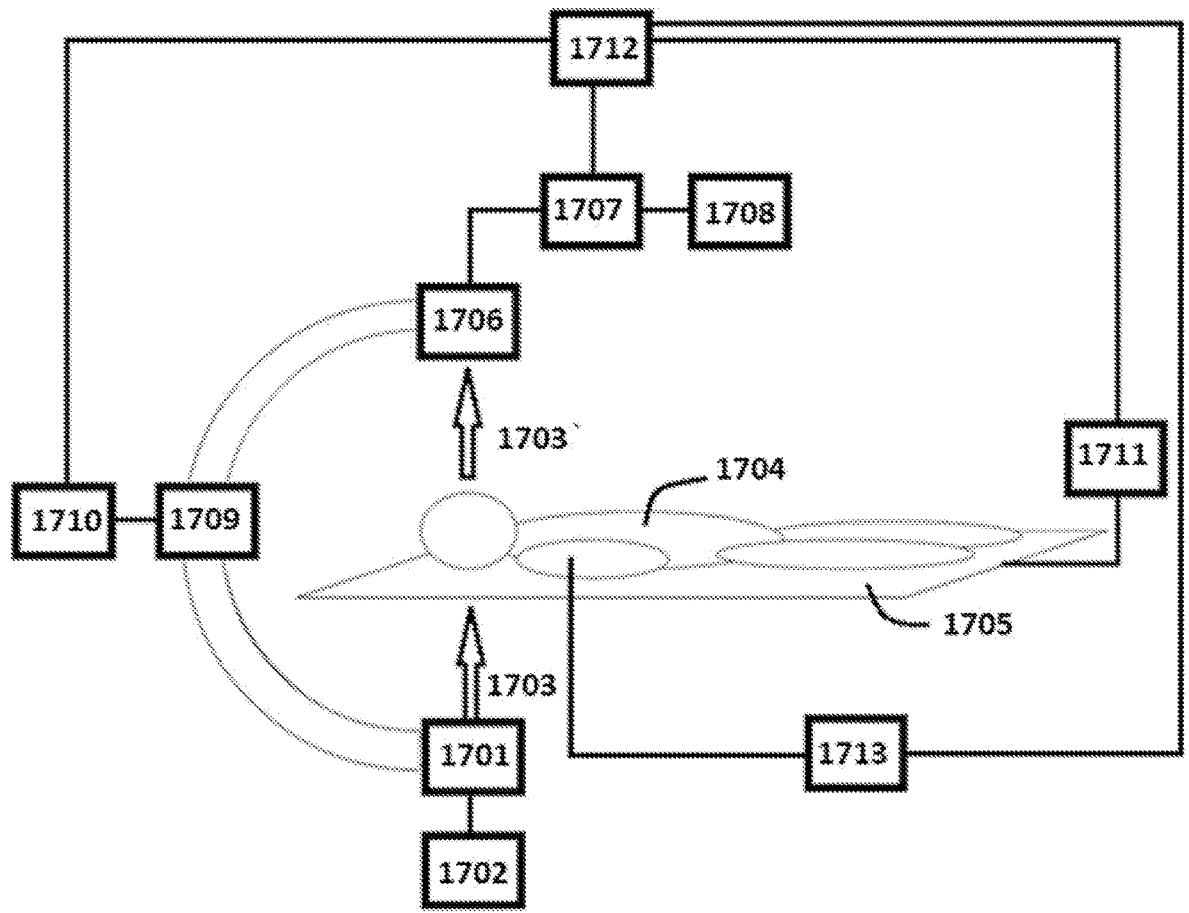
FIG. 17 is a block diagram of an exemplary x-ray cine-fluorographic unit in accordance with an embodiment herein.

Operations can be performed by processor unit on a standalone system or included directly in, for instance, an x-ray fluorographic system or any other image system to acquire two dimensional angiographic image sequences. FIG. 17 illustrates an example of a high-level block diagram of an x-ray cinefluorograpic system. In this block diagram an example is shown on how embodiments could integrate in such a system.

Portions of the system (as defined by various functional blocks) may be implemented with dedicated hardware, analog and/or digital circuitry, and/or one or more processors operating program instructions stored in memory.

The X-ray system of FIG. 17 includes an X-ray tubes 1701 with a high voltage generator 1702 that generates an X-ray beam 1703.

The high voltage generator 1702 controls and delivers power to the X-ray tube 1701. The high voltage generator 1702 applies a high voltage across the vacuum gap between the cathode and the rotating anode of the X-ray tube 1701.

Due to the voltage applied to the X-ray tube 1701, electron transfer occurs from the cathode to the anode of the X-ray tube 1701 resulting in X-ray photon-generating effect also called Bremsstrahlung. The generated photons form an X-ray beam 1703 directed to the image detector 1706.

An X-ray beam 1703 comprises of photons with a spectrum of energies that range up to a maximum determined by among others the voltage and current submitted to the X-ray tube 1701.

The X-ray beam 1703 then passes through the patient 1704 that lies on an adjustable table 1705. The X-ray photons of the X-ray beam 1703 penetrate the tissue of the patient to a varying degree. Different structures in the patient 1704 absorb different fractions of the radiation, modulating the beam intensity.

The modulated X-ray beam 1703' that exits from the patient 1704 is detected by the image detector 1706 that is located opposite of the X-ray tube. This image detector 1706 can either be an indirect or a direct detection system.

In case of an indirect detection system, the image detector 1706 comprises of a vacuum tube (the X-ray image intensifier) that converts the X-ray exit beam 1703' into an amplified visible light image. This amplified visible light image is then transmitted to a visible light image receptor such as a digital video camera for image display and recording. This results in a digital image signal.

In case of a direct detection system, the image detector 1706 comprises of a flat panel detector. The flat panel detector directly converts the X-ray exit beam 1703' into a digital image signal.

The digital image signal resulting from the image detector 1706 is passed through a digital image processing unit 1707. The digital image processing unit 1707 converts the digital image signal from 1706 into a corrected X-ray image (for instance inverted and/or contrast enhanced) in a standard image file format for instance DICOM. The corrected X-ray image can then be stored on a hard drive 1708.

Furthermore the X-ray system of FIG. 17 comprises of a C-arm 1709. The C-arm holds the X-ray tube 1701 and the image detector 1706 in such a manner that the patient 1704 and the adjustable table 1705 lie between the X-ray tube 1701 and the image detector 1706. The C-arm can be moved (rotated and angulated) to a desired position to acquire a certain projection in a controlled manner using the C-arm control 1710. The C-arm control allows for manual or automatic input for adjustment of the C-arm in the desired position for the X-ray recording at a certain projection.

The X-ray system of FIG. 17 can either be a single plane or a bi-plane imaging system. In case of a bi-plane imaging system, multiple C-arms 1709 are present each consisting of an X-ray tube 1701, an image detector 1706 and a C-arm control 1710.

Additionally, the adjustable table 1705 can be moved using the table control 1711. The adjustable table 1705 can be moved along the x, y and z axis as well as tilted around a certain point.

Furthermore a measuring unit 1713 is present in the X-ray system. This measuring unit contains information regarding the patient that is an input for the calculations, for instance information regarding aortic pressure, biomarkers, and/or height, length etc.

A general unit 1712 is also present in the X-ray system. This general unit 1712 can be used to interact with the C-arm control 1710, the table control 1711, the digital image processing unit 1707, and the measuring unit 1713.

An embodiment is implemented by the X-ray system of FIG. 17 as follows. A clinician or other user acquires at least two X-ray angiographic image sequences of a patient 1704 by using the C-arm control 1710 to move the C-arm 1709 to a desired position relative to the patient 1704. The patient 1704 lies on the adjustable table 1705 that has been moved by the user to a certain position using the table control 1711.

The X-ray image sequences are then generated using the high voltage generator 1702, the X-ray tube 1701, the image detector 1706 and the digital image processing unit 1707 as described above. These images are then stored on the hard drive 1708. Using these X-ray image sequences, the general processing unit 1712 generates a 3D reconstruction, determines geometrical information, determines lesion position(s) and calculates hemodynamic results based on patient specific data. The general processing unit 1712 determines the hemodynamic results using the information of the measuring unit 1713.

There have been described and illustrated herein several embodiments of a method and apparatus for quantitative flow analysis. While particular embodiments have been described, it is not intended that the invention be limited thereto, as it is intended that the invention be as broad in scope as the art will allow and that the specification be read likewise. For example, the data processing operations can be performed offline on images stored in digital storage. This is typically done in a universal language (vendor independent) such as DICOM (Digital Imaging and Communications in Medicine). The storage can be a hard disk or a PACS (picture archiving and communications system) server or a VNA (vendor neutral archive) or other picture archiving and communication systems commonly used in the medical imaging arts. It will therefore be appreciated by those skilled in the art that yet other modifications could be made to the provided invention without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

While the disclosed embodiments are described with respect to a single or biplane X-ray imaging modality, variations within these embodiments are also applicable for 3D reconstructions for instance based on rotational angiography, computed tomography, magnetic resonance imaging and the like.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

REFERENCES

US2017236326, Method and Apparatus for User Guidance for the Choice of a Two-Dimensional Angiographic Projection.

U.S. Pat. No. 7,155,046, Method of Determining Physical Parameters of Bodily Structures.

EP3403582, Method and apparatus for determining blood velocity in X-ray angiography images.

M. J. Kern, P. S. Sorajja, M. J. Lim, "*Cardiac Catheterization Handbook, 6th Edition*", Elsevier Chapter 10 "Interventional Cardiology Procedures" page 424.

Gould and et al., "Physiologic basis for assessing critical coronary stenosis. Instantaneous flow response and regional distribution during coronary hyperemia as measures of coronary flow reserve", Am J Cardiol. 1974 January; 33(1):87-94.

Shipilfoygel et al, "X-ray videodensitometric methods for blood flow and velocity measurement: A critical review of literature", Medical Physics vol 27, No. 9, September 2000.

Ofili et al., "Differential characterization of blood flow, velocity, and vascular resistance between proximal and distal normal epicardial human coronary arteries: Analysis by intracoronary Doppler spectral flow velocity", American Heart Journal. 1995 July; 130(1):37-46.

Girasis C, et al, "Advanced three-dimensional quantitative coronary angiographic assessment of bifurcation lesions: methodology and phantom validation", EuroIntervention 2013; 8: 1451-1460

Gronenschild E, et al. in "CAAS II: A Second Generation system for Off-Line and On-Line Quantitative Coronary Angiography", Cardiovascular Diagnosis 1994; 33: 61-75.

Jonathan S, et al., "Blood-Pressure Measurement", N Engl J Med 2009; 360:e6.

Robert M, et al., "Cardiovascular Physiology, Eight Edition".

Härle T, et al., "Influence of hydrostatic pressure on intracoronary indices of stenosis severity in vivo", Clin Res Cardiol 2018107:222-232

Wentzel et al. Geometry guided data averaging enables the interpretation of shear stress related plaque development in human coronary arteries. Journal of Biomechanics 2005, 1551-1555.

Fischer et al., "*Non-rigid image registration*", In: http://www.miC.uni-luebeck.de/uploads/tx_wapublications/2006-KOREA-BF.pdf, 2006

Shi et al. "Review of Zero-D and 1-D Models of Blood Flow in the cardiovascular System", BioMedical Engineering OnLine (2011) 10:33

Pijls et al., "Coronary Pressure Measurement After Stenting Predicts Adverse Events at Follow-Up" circulation 2002: 105:2950-2954.

Sezer M., "New Mathematical Correction Model in Pursuit of Optimal Hemodynamic Assessment of Serial Coronary Artery Disease: Overcoming Hyperemic Cross Talk Between Coronary Stenoses in Series," J Am Heart Association 2018 Oct. 16; 7(20).

Vogelzang et al. "Computer-assisted myocardial blush quantification after percutaneous coronary angioplasty for acute myocardial infarction: a substudy from the TAPAS trial", European Heart Journal (2009) 30, 594-599.

Kirkeeide et al., "Assessment of coronary stenoses by myocardial perfusion imaging during pharmacologic coronary vasodilation. VII. Validation of coronary flow reserve as a single integrated functional measure of stenosis severity reflecting all its geometric dimensions", J Am Coll Cardiol. 1986 January; 7(1):103-13.

All references, including publications, patent applications and patents, cited herein are hereby incorporated by reference to the same extent as if each reference were individually and specifically indicated to be incorporated by reference and were set forth in its entirety herein.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

What is claimed is:

1. A computer-implemented method for quantitative hemodynamic flow analysis, comprising:
    retrieving patient specific image data;
    creating a 3D reconstruction of a vessel of interest from the patient specific image data;
    determining at least one of an area or diameter along at least a portion of the vessel of interest based on the 3D reconstruction, the vessel of interest includes a lesion segment related to a lesion;
    determining a position of the lesion segment;
    estimating at least one of a healthy reference area or healthy reference diameter along at least a portion of the vessel of interest, the estimating including:
        creating a histogram of at least one of area or diameter data points along at least the portion of the vessel of interest;
        discarding the area or diameter data points that are below a threshold value; and
        utilizing remaining area or diameter data points to estimate the at least one of the healthy reference area or healthy reference diameter along at least the portion of the vessel of interest; and
    calculating at least one of a predicted pressure change or predicted fractional flow reserve (FFR) to result from removal of the lesion in the lesion segment based on the at least one of healthy reference area or diameter.

2. The method of claim 1, wherein at least one of the operations is performed by one or more processors executing program instructions.

3. The method of claim 1, wherein the determining of the lesion position is based, at least in part, on calculation of a flow pattern parameter indicative of whether flow is laminar or turbulent, wherein the flow pattern parameter is calculated based on the healthy reference area or healthy reference diameter.

4. The method of claim 3, wherein the flow pattern parameter is a Reynolds number.

5. The method of claim 1, wherein the determining of the lesion position involves identifying variation in blood velocity along the vessel of interest wherein the variation is caused by a presence of vessel narrowing.

6. The method of claim 5, wherein the variation in the blood velocity is calculated based on the healthy reference area or healthy reference diameter.

7. The method of claim 1, further comprising:
calculating a friction estimate to be experienced by blood flow through a stent placed in the lesion segment; and
calculating the predicted pressure change based in part on the friction estimate.

8. The method of claim 1, wherein:
the vessel of interest represents a subset of a coronary tree; and
the calculating is based in part on an assumption that the coronary tree exhibits a constant healthy velocity throughout.

9. The method of claim 1, further comprising:
calculating an initial pressure resulting from the lesion in the lesion segment based on the at least one of the area or diameter, wherein the predicted pressure change is based in part on the initial pressure.

10. The method of claim 1, further comprising:
calculating a gravitational pressure gradient due to a difference in altitude along proximal and distal ends of the vessel of interest, wherein the at least one of predicted pressure change or FFR are calculated in part based on the gravitational pressure gradient.

11. The method of claim 1, wherein the calculating the predicted pressure change along the vessel of interest includes calculating at least one of i) pressure gradients due to viscous effects or ii) pressure gradient due to separation effects.

12. The method of claim 11, wherein at least one of the viscous effects or separation effects are calculated based on the healthy reference area or healthy reference diameter.

13. The method of claim 9, wherein the calculating further comprises:
determining at least one of an area curve or a diameter curve indicative of variation in area or diameter along the vessel of interest;
calculating an initial pressure based on at least one of the area curve or the diameter curve;
automatically replacing a portion of the area curve or diameter curve corresponding to the lesion segment with at least one of the healthy reference area or health reference diameter;
calculating an updated pressure based on the portion replaced with at least one of the healthy reference area or health reference diameter; and
determining the predicted pressure change based on the initial and updated pressures, without modification of the 3D reconstruction of the vessel of interest.

14. The method of claim 1, wherein the calculating further comprises:
determining a patient specific hyperemic constant velocity based on the area or diameter along the vessel of interest and the healthy reference area or healthy reference diameter along at least a portion of the lesion segment.

15. The method of claim 1, further comprising:
calculating a virtual pullback of a pressure drop along the vessel of interest within the 3D reconstruction;
calculating a virtual pullback curve;
utilizing geometrical information of a segment to calculate the predicted pressure drop and predicted FFR between first and second locations along the vessel of interest; and
adding the predicted pressure drop and predicted FFR to pullback curve data corresponding the second location.

16. The method of claim 1, wherein the estimating further comprising dynamically determining the threshold value.

17. A system for quantitative hemodynamic flow analysis, comprising:
at least one processor, that when executing program instructions, is configured to:
retrieve patient specific image data;
create a 3D reconstruction of a vessel of interest from the patient specific image data;
determine at least one of an area or diameter along at least a portion of the vessel of interest based on the 3D reconstruction, the vessel of interest includes a lesion segment related to a lesion;
determine a position of the lesion segment;
estimate at least one of a healthy reference area or healthy reference diameter along at least a portion of the vessel of interest, the estimate including to:
create a histogram of at least one of area or diameter data points along the portion of the vessel of interest;
discard the area or diameter data points that are below a threshold value; and
utilize remaining area or diameter data points to estimate the at least one of the healthy reference area or healthy reference diameter along at least the portion of the vessel of interest; and
calculate at least one of a predicted pressure drop or predicted fractional flow reserve (FFR) to result from removal of the lesion in the lesion segment based on the at least one of healthy reference area or diameter.

18. The system of claim 17, wherein the at least one processor is further configured to determine the lesion position based, at least in part, on calculation of a flow pattern parameter indicative of whether flow is laminar or turbulent, wherein the flow pattern parameter is calculated based on the healthy reference area or healthy reference diameter.

19. The system of claim 18, wherein the flow pattern parameter is a Reynolds number.

20. The system of claim 17, wherein the at least one processor is further configured to determine the lesion position by identifying variation in blood velocity along the vessel of interest wherein the variation is caused by a presence of vessel narrowing.

21. The method of claim 20, wherein the at least one processor is further configured to calculate the variation in the blood velocity based on the healthy reference area or healthy reference diameter.

22. The system of claim 17, wherein the at least one processor is further configured to:
calculate a friction estimate to be experienced by blood flow through a stent placed in the lesion segment; and
calculate the predicted pressure change based in part on the friction estimate.

23. The system of claim 17, wherein the vessel of interest represents a subset of a coronary tree; and wherein the at least one processor is further configured to perform the calculating based in part on an assumption that the coronary tree exhibits a constant healthy velocity throughout.

24. The system of claim 17, wherein the at least one processor is further configured to:
calculate an initial pressure resulting from the lesion in the lesion segment based on the at least one of the area or diameter, wherein the predicted pressure change is based in part on the initial pressure.

25. The system of claim 17, wherein the at least one processor is further configured to calculate a gravitational pressure gradient due to a difference in altitude along proximal and distal ends of the vessel of interest, wherein the at least one of predicted pressure change or FFR are calculated in part based on the gravitational pressure gradient.

26. The system of claim 17, wherein the at least one processor is further configured to: calculate the predicted pressure drop along the vessel of interest by calculating at least one of i) pressure gradients due to viscous effects or ii) pressure gradient due to separation effects.

27. The system of claim 26, wherein the at least one processor is further configured to calculate at least one of the viscous effects or separation effects based on the healthy reference area or healthy reference diameter.

28. The system of claim 17, wherein the at least one processor is further configured to:
- determine at least one of an area curve or a diameter curve indicative of variation in area or diameter along the vessel of interest;
- calculate an initial pressure based on at least one of the area curve or the diameter curve;
- automatically replace a portion of the area curve or diameter curve corresponding to the lesion segment with at least one of the healthy reference area or health reference diameter;
- calculate an updated pressure based on the portion replaced with at least one of the healthy reference area or health reference diameter; and
- determine the predicted pressure change based on the initial and updated pressures, without modification of the 3D reconstruction of the vessel of interest.

29. The system of claim 17, wherein the at least one processor is further configured to:
- determine a patient specific hyperemic constant velocity based on the area or diameter along the vessel of interest and the healthy reference area or healthy reference diameter along at least a portion of the lesion segment.

30. The system of claim 17, wherein the at least one processor is further configured to:
- calculate a virtual pullback of a pressure drop along the vessel of interest within the 3D reconstruction;
- calculate a virtual pullback curve;
- utilize geometrical information of a segment to calculate the predicted pressure drop and predicted FFR between first and second locations along the vessel of interest; and
- add the predicted pressure drop and predicted FFR to pullback curve data corresponding the second location.

31. The system of claim 17, wherein the at least one processor is further configured to dynamically determine the threshold value.

* * * * *